(12) United States Patent
Marx et al.

(10) Patent No.: US 8,759,061 B1
(45) Date of Patent: Jun. 24, 2014

(54) MUTATED DNA POLYMERASES WITH INCREASED MISPAIRING DISCRIMINATION

(75) Inventors: Andreas Marx, Constance (DE); Daniel Summerer, Mannheim (DE); Nicolas Zackes Rudinger, Köln (DE)

(73) Assignee: Rheinische Friedrich-Wilhelms-Universitaet Bonn, Bonn (DE)

( * ) Notice: Subject to any disclaimer, the term of this patent is extended or adjusted under 35 U.S.C. 154(b) by 2111 days.

(21) Appl. No.: 10/588,570

(22) PCT Filed: Feb. 4, 2005

(86) PCT No.: PCT/EP2005/050479
§ 371 (c)(1),
(2), (4) Date: May 4, 2007

(87) PCT Pub. No.: WO2005/074350
PCT Pub. Date: Aug. 18, 2005

(30) Foreign Application Priority Data

Feb. 5, 2004  (DE) .......................... 10 2004 005 885

(51) Int. Cl.
*C12N 9/12* (2006.01)
*C12P 19/34* (2006.01)

(52) U.S. Cl.
USPC ....... 435/194; 435/91.2; 435/183; 435/252.3; 435/320.1; 536/23.1; 530/350

(58) Field of Classification Search
None
See application file for complete search history.

(56) References Cited

PUBLICATIONS

Ngo et al., in The Protein Folding Problem and Tertiary Structure Prediction, 1994, Merz et al. (ed.), Birkhauser, Boston, MA, pp. 433 and 492-495.*
Minnick, Dana T., et al., "Side Chains That Influence Fidelity at the Polymerase Active Site of *Escherichia coli* DNA Polymerase I (Klenow Fragment)," *The Journal of Biological Chemistry*, 274(5):3067-3075, Jan. 29, 1999.
Pavlov, Andrey R., et al., "Recent developments in the optimization of thermostable DNA polymerases for efficient applications," *TRENDS in Biotechnology*, 22(5):253-260, May 2004.
Patel, Premal H., et al., "Prokaryotic DNA Polymerase I: Evolution, Structure, and "Base Flipping" Mechanism for Nucleotide Selection," *J. Mol. Biol.*, 308:823-837, 2001.

* cited by examiner

*Primary Examiner* — Richard Hutson
(74) *Attorney, Agent, or Firm* — Seed IP Law Group PLLC

(57) ABSTRACT

The present invention relates to DNA polymerases with a special mutation which have an enhanced mismatch discrimination, the preparation and use thereof. The thermostable DNA polymerases with this mutation are particularly suitable for diagnostic and molecular-biological methods, e.g., allele-specific PCR.

27 Claims, 5 Drawing Sheets

MUTATED DNA POLYMERASES WITH INCREASED MISPAIRING DISCRIMINATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 63096_401USPC_SEQUENCE_LISTING.txt. The text file is 52 KB, was created on Feb. 9, 2011, and is being submitted electronically via EFS-Web.

The present invention relates to DNA polymerases with a special mutation which have an enhanced mismatch discrimination, the preparation and use thereof. The thermostable DNA polymerases with this mutation are particularly suitable for diagnostic and molecular-biological methods, e.g., allele-specific PCR.

BACKGROUND OF THE INVENTION

Since the first human genome sequences were presented, the research has been focused on the discovery of genetic differences between individuals, such as single-base mutations ("single nucleotide polymorphisms", SNPs). This is of interest because it becomes more and more evident that single-base variations in the genome are associated with different drug tolerances or predisposition for a wide variety of diseases. In the future, the knowledge of medically relevant nucleotide variations could allow to adapt therapies to the individual genetic supply, and treatment with medicaments which are ineffective or even cause side effects could be prevented (Shi, Expert Rev. Mol. Diagn. 1, 363-365 (2001)). It is obvious that developments which enable a time- and cost-efficient identification of nucleotide variations lead to further progress in pharmacogenetics.

SNPs account for the majority of genetic variations in the human genome and are the cause of more than 90% of the differences between individuals (Kwok, Annu. Rev. Genomics Hum, Genet. 2, 235-258 (2001); Kwok and Chen, Curr. Issues Mol. Biol. 5, 43-60 (2003); Twyman and Primrose, Pharmacogenomics 4, 67-79 (2003)). To detect such genetic variations and other nucleic acid variants, such as mutations, various methods can be employed. For example, the identification of a variant of a target nucleic acid can be effected by hybridizing the nucleic acid sample to be analyzed with a hybridization probe specific for the sequence variant under suitable hybridization conditions (Guo et al., Nat. Biotechnol. 15, 331-335 (1997)).

However, it has been found that such hybridization methods fail to meet, in particular, the clinical requirements in terms of the necessary sensitivity of such assays. Therefore, especially PCR has also found broad use in molecular-biological and diagnostic examination methods for the detection of mutations, single-nucleotide polymorphisms (SNPs) and other allelic sequence variants (Saiki et al., Science 239, 487-490 (1988)), wherein a target nucleic acid to be examined in view of the existence of a variant is amplified by a polymerase chain reaction prior to hybridization. As hybridization probes for such assays, single-strand oligonucleotides are usually used. A modified embodiment of such assays includes those which employ fluorescent hybridization probes (Livak, Genet. Anal. 14, 143-149 (1999)). Generally, it is sought to automate methods for the determination of SNPs and other sequence variations (Gut, Hum. Mutat. 17, 475-492 (2001)).

An alternative of sequence variant specific hybridization which is already known in the prior art is offered by the so-called allele-specific amplification (Newton et al., Nucleic. Acids Res. 17, 2503-2516 (1989); Germer et al., genome res. 10, 258-266 (2000); Gibbs et al., Nucleic. Acids Res. 17, 2437-2448 (1989); Wu et al., PNAS 86, 2757-2769 (1989); Ishikawa et al., Hum. Immunol. 42, 315-318 (1995)). In this detection method, already during the amplification, variant-specific amplification primers are employed which usually have a so-called discriminating terminal nucleotide residue at the 3'-terminal end of the primer, which residue is merely complementary to only one specific variant of the target nucleic acid to be, detected. In this method, nucleotide variations are determined by the presence or absence of DNA product after PCR amplification. The principle of allele-specific amplification is based on the formation of canonical or non-canonical primer-template complexes at the end of allele-specific primer probes. At a correctly paired 3' primer end, the amplification by a DNA polymerase can occur, while at a mismatched primer end, extension should be inhibited.

For example, U.S. Pat. No. 5,595,890 describes such methods for allele-specific amplification and their application for the detection of clinically relevant point mutations, for example, in the k-ras oncogene. U.S. Pat. No. 5,521,301 also describes methods for allele-specific amplification for the genotyping of the ABO blood group system. In contrast, U.S. Pat. No. 5,639,611 discloses the use of allele-specific amplification in connection with the detection of the point mutation responsible for sickle-cell anemia.

However, allele-specific amplification is problematic in that it is characterized by a low selectivity, which necessitates further complicated and thus time- and cost-intensive optimization steps.

Such methods for detecting sequence variants, polymorphisms and mainly point mutations require allele-specific amplification especially when the sequence variant to be detected is deficient as compared with a predominant variant of the same nucleic acid segment (or of the same gene).

For example, such a situation occurs if disseminated tumor cells are to be detected in body fluids, such as blood, serum or plasma, by means of allele-specific amplification (U.S. Pat. No. 5,496,699). For this purpose, DNA is first isolated from body fluids such as blood, serum or plasma, which DNA is composed of a deficiency of DNA from disseminated tumor cells and an excess of DNA from non-proliferating cells. Thus, the mutations in the k-ras gene significant for tumoral DNA must be detected from a few copies of tumoral DNA in the presence of an excess of wild type DNA.

All the methods for allele-specific amplification described in the prior art have the disadvantage that, despite the use of 3'-discriminating nucleotide residues, a primer extension occurs to a lower extent in the presence of a suitable DNA polymerase even if the target nucleic acid does not exactly correspond to the sequence variant to be detected, i.e., is distinguished therefrom at least by the nucleotide complementary to the nucleotide residue to be discriminated. This leads to false-positive results especially if a particular sequence variant is to be detected in an excess background of nucleic acids containing another sequence variant. As mentioned above, this is the case, for example, in the detection of particular k-ras alleles as indicators of disseminated tumor cells. Another disadvantage of the known methods is the fact that a 3'-terminally discriminating oligonucleotide residue must be used at any rate. The main reason for the disadvantages of these PCR-based methods is the incapability of the polymerases employed in these methods to sufficiently discriminate between base mismatches. Therefore, it has not yet been possible by PCR to directly obtain unambiguous information about the presence or absence of a mutation. To date, further time- and cost-intensive purification and analytical methods have always been necessary for an unambiguous diagnosis of such mutations. Therefore, novel methods which enable an enhancement of the selectivity of allele-specific PCR amplification will have a significant impact on the reliability and robustness of direct SNP analysis by PCR.

On the other hand, a number of modifications have already been described in the protein sequence of DNA polymerases I. Thus, U.S. Pat. No. 6,329,178 mentions DNA polymerase mutants with altered catalytic activity in which there were mutations in the A motif (the highly conserved sequence DYSQIELR (SEQ ID NO:38)). In addition, Minnick, T. et al., J. Biol. Chem. 274, 3067-3075 (1999), describe a wide variety of E. coli DNA polymerase I (Klenow fragment) mutants in which alanine exchanges have been performed. Part of the mutants described exhibit a higher polymerase accuracy as compared to the wild type. One of the mutants mentioned is H881A; particular properties of these mutants with respect to the other mutants described are not stated.

Therefore, it was the object of the present invention to provide sequence variants with enhanced specificity by means of which a sequence variant specific detection method is enabled.

SUMMARY OF THE INVENTION

Surprisingly, it has been found that special mutants of family A DNA polymerases, namely those in which the conserved C motif and especially its QVH amino acid sequence has been modified, exhibit an enhanced mismatch discrimination and can be employed in detection methods for sequence variants. The thermostable variants thereof are suitable for allele-specific PCR. In detail, the present invention relates to:

(1) a family A DNA polymerase which has a modified motif C sequence and an enhanced mismatch discrimination as compared to the corresponding wild type polymerase, or a Klenow fragment thereof;

(2) a preferred DNA polymerase of embodiment (1), wherein in the motif C sequence QVH in positions 879-881, based on the E. coli DNA polymerase Klenow fragment shown in SEQ ID NO: 2, at least the amino acid residue Q879 has been replaced by a lipophilic amino acid residue;

(3) a DNA sequence which encodes said DNA polymerase or the Klenow fragment thereof according to embodiment (1) or (2);

(4) a vector which contains the DNA sequence according to embodiment (3);

(5) a host cell which has been transformed with the vector according to embodiment (4) and/or includes a DNA according to embodiment (3);

(6) a process for the preparation of a DNA polymerase or its Klenow fragment according to embodiment (1) or (2), which comprises culturing a host cell according to embodiment (5) and isolating the DNA polymerase or the Klenow fragment from the culture or the culture supernatant;

(7) the use of the DNA polymerase or the Klenow fragment according to embodiment (1) or (2) in diagnostic and molecular-biological methods including allele-specific PCR, DNA amplification by means of PCR, cloning, etc.;

(8) a method for determining the presence or absence of at least one sequence variant in one or more target nucleic acids in an individual sample using a DNA polymerase according to embodiment (1) or (2); and (9) a kit for determining the presence or absence of at least one sequence variant in one or more target nucleic acids in an individual sample according to the method of embodiment (8), containing at least one DNA polymerase according to embodiment (1) or (2).

a: primer probe: 5'-d(GAC CCA CTC CAT CGA GAT TTC T) (SEQ ID NO: 19);

reverse primer: 5'-d(AGA GGA AAG ATG AAG TAC TAT G) (SEQ ID NO: 20);

template: 5'-d(CAA CTG TTC AAA CTG ATG GGA CCC ACT CCA TCG AGA TTT CXC TGT AGC TAG ACC AAA ATC ACC TAT TTT TAC TGT GAG GTC TTC ATG AAG AAA TAT ATC TGA GGT GTA GTA AGT AAA GGA AAA CAG TAG ATC TCA TTT TCC TAT CAG AGC MG CAT TAT GAA GAG TTT AGG TTT GAG ATC TAA TTT CTA TAA TTC TGT MT ATA ATA TIC TTT AAA ACA TAG TAC TTC ATC TTT CCT CT), X=A (wild type) (1) or T (mutant) (2) (SEQ ID NO: 21).

b: primer probe: 5'-d(GTT TTA GAT GT TAA ATC ACA CTT AT) (SEQ ID NO: 22);

reverse primer: 5-d(AAA GCT CCT TTC TGA ATA TTG AG) (SEQ ID NO: 23);

template: 5'-d(AAA ATG TGA GM GGG ACC TCA TAA AAT ATG TCA TAT GGA AAT GAG CAG ATA ATA AAG ATT ATA GCT TTT CTT TGT CAA AAG GAG ACT CAA TAT CTT TAC TCT TIC ATC AGG ACA TTG TGA CAA ATG TTT CCC CCA GAA TCA TCC GGG GAA CCA CCT CTG GCC CCA TGT ATG GCC CTG GAC AAA GCT CCT TTC TGA ATA TTG AGC TCA TCA GTG AGA AAA CGG CTG CAT ATT GGT GTC AAA GTG TCA CTG AAC TAA AGG CTG ACT TTC CAG ACA ACX TAA GTG TGA TTT AAC ATC TAA AAC), X=A (wild type) (3) or G (mutant) (4) (SEQ ID NO: 24).

Figure 5:
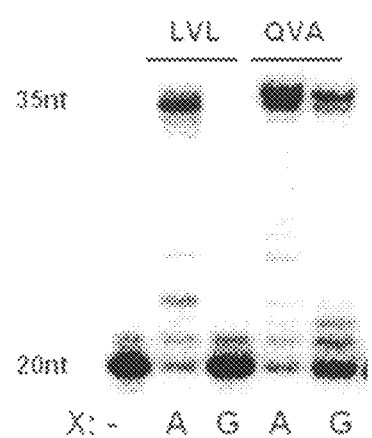

FIG. 5: Autoradiographs after denaturing PAGE for a comparative examination of the influence of mutations in *E. coli* DNA polymerase I (Klenow fragment, 5'→3' exonuclease-deficient) in positions 879-881 (SEQ ID NO; 2) on the selectivity of primer extension. The mutant LVL according to the invention was compared with the mutant QVA known from the literature (Minnick, T. et al., J. Biol. Chem. 274, 3067-3075 (1999)). Reactions contained 150 nM primer/template complex (primer: 5'-ACA AAA TAC CTG TAT TCC TX-3 X=A, G, C or T (SEQ ID NO: 11); template: 5'-GA TCC CTG GAC AGG CYA GGA ATA CAG GTA TTT TGT-3 Y=A, G, C or T (SEQ ID NO: 12), 1 mM each of dATP, dCTP, TTP, dGTP, and 600 nM DNA polymerase. Incubation at 37° C. for 10 min in buffer (50 mM Iris-HCl, pH 7.3, 10 mM MgCl$_2$, 1 mM DTT, 0.05% Triton® X-100).

| Sequence listing - free text | |
|---|---|
| SEQ ID NO: | Description - free text |
| 1 | *E. coli* wild type Klenow fragment of DNA polymerase 1 |
| 2 | *E. coli* Klenow fragment of DNA polymerase 1 |
| 3 | wild type Taq polymerase |
| 4 | wild type Taq polymerase |
| 5 | primer |
| 6 | downstream primer |
| 7 | antisense primer |
| 8 | primer FVL20TH |
| 9 | template TFVL90A |
| 10 | template TFVL90G |
| 11 | primer for the detection of SNP in the human genomic factor V Leiden DNA sequence |
| 12 | template of the human genomic factor V Leiden DNA sequence; n = g, wild type template; n = a, mutant template |
| 13 | primer for the detection of human somatic BRAF-T1796A mutation |

| Sequence listing - free text | |
|---|---|
| SEQ ID NO: | Description - free text |
| 14 | wild type template of the BRAF gene; w = t, wild type template; w = a, mutant template |
| 15 | primer for the detection of human dihydropyrimidine dehydrogenase (DPyD) mutation G735A |
| 16 | template of the human DPyD; r = g, wild type template; r = a, mutant template |
| 17 | primer for the detection of human acid ceramidase mutation A107G |
| 18 | template of human acid ceramidase; r = a, wild type template; r = g, mutant template |
| 19 | primer probe BrafT |
| 20 | reverse primer for BRAF |
| 21 | target template BrafX; w = a, Braf A (wild type); w = t, BrafT (mutant) |
| 22 | primer probe DpyDT |
| 23 | reverse primer for DpyDT |
| 24 | target template DpyDX; r = a, DpyDA (wild type); r = t, DpyDT (mutant) |
| 25 | pTTQ18::Taq |
| 26 | pQE30 |
| 27 | template segment (SEQ ID NO: 14); w = t, wild type; w = a, mutant template |
| 28 | template segment (SEQ ID NO: 16); r = g, wild type; r = a, mutant |
| 29 | template segment (SEQ ID NO: 12); r = t, wild type; r= a, mutant |

DETAILED DESCRIPTION OF THE INVENTION

The present invention relates to mutant family A DNA polymerases having an enhanced capability of mismatch discrimination, or Klenow fragments thereof. The enhanced capability of mismatch discrimination, which means a high selectivity according to the Watson-Crick rules during the incorporation of complementary bases and also already during the annealing of a primer to the template, i.e., a higher extension selectivity ratio ($F_{march}/F_{mismatch}$) as compared to the corresponding starting polymerase (wild type) (e.g., determined in a fluorescence test system according to Example 2), can be achieved by mutating a particular amino acid sequence in natural enzymes. The properties of DNA polymerases caused thereby are superior to those of the "state of the art" wild type polymerases as currently sold commercially. The enhancement of the selectivity of the activity of DNA polymerases enables more reliable systems for detecting mutations or polymorphisms, a direct diagnosis by allele-specific PCR without downstream time- and cost-intensive purification and analytical methods, and a high sustainability because no chemically modified primers need to be used.

The following definitions are to be applied to the whole application, they are however not to be construed as limiting the invention. "Family A DNA polymerases" (also referred to as "polymerases I") are those DNA-polymerizing enzymes which contain the A motif with the sequence DYSQIELR (SEQ ID NO:38) in their active site. They also include the enzymes described herein which have mutations in the C motif. In particular, they also include thermostable DNA polymerases and their mutants.

The term "Klenow fragment" as used herein means any C-terminal fragment of a family A DNA polymerase which has both polymerase activity and exonuclease activity (but no 5'→3' exonuclease activity). "Vectors" as used herein include plasmids, cosmids, phagemids and viruses which, in addition of a DNA of interest (which are, in particular, sequences of family A DNA polymerases according to the invention), also include regulation elements which control the expression of the DNA of interest.

The term "host cells" includes both prokaryotic cells, such as E. coli (especially E. coli XL1-blue, DH5α, Bl21 (DE3), M15 [pREP4], SG13005 [pREP4], BL21 (DE3) pLysS), Halomonas elongata, Caulobacter sp., Halobacterium halobium etc., and eukaryotic cells, such as yeast and other fungal cells, plant and animal cells including isolated human cells in cell culture. Further, the term "host cell" also relates to cell extracts which, when presented an mRNA, are able to translate it, such as wheat germ extract and rabbit reticulocyte extract (RRL). Further, "host cell" also includes in vitro expression systems, such as T7 Expression System, pBAD Expression System, ThioFusion™ Expression Systems, trc Expression System, PL Expression System, PurePro™ Caulobacter Expression System, Microbiological Media and Media Components, Qiagen pQE Expression System and Novagen pET Expression System, etc.

Embodiments (1) and (2) of the invention relate to family A DNA polymerases or their Klenow fragment which are distinguished from naturally occurring DNA polymerases by having an enhanced mismatch discrimination, which results in an increased selectivity of enzyme activity. The DNA polymerases according to the invention are derived from bacterial DNA polymerases, such as polymerases from E. coli, Aquifex, Borrelia, Bacillus, Chlamydia, Chlamydophila, Chloroflexus, Haemophilus, Heliobacter, Lactococcus, Methylobacterium, Mycobacterium, Rhodothermus, Rickettsia, Streptococcus, Streptomyces, Synechocystis, Treponema etc., but also, in particular, from polymerases of thermostable organisms, such as Thermus aquaticus, Thermus thermophilus, Thermus filiformis, Rhodothermus obamensis, Bacillus stearothermophilus etc. In particular, in the DNA polymerases according to embodiment (1) of the invention or their Klenow fragments, at least one amino acid residue, preferably Q and/or H, in the motif C sequence QVH in positions 879-881 (based on the E. coli DNA polymerase Klenow fragment shown in SEQ ID NO: 2) has been replaced by a lipophilic amino acid residue.

In embodiment (2) of the invention, at least the amino acid residue Q879, based on SEQ ID NO: 2, has been replaced by a lipophilic amino acid residue. In a preferred aspect of embodiment (2), the amino acid residue H881 in the motif C sequence QVH has been further replaced by a lipophilic amino acid residue.

In a further preferred aspect of embodiments (1) and (2), the amino acid residue in position 880 (based on SEQ ID NO: 2) is selected from Val, Leu, Ile, Ala and Tyr, more preferably from Val and Ile.

"Lipophilic amino acid residues" within the meaning of the present invention comprise the amino acid residues Gly, Ala, Val, Leu, Met, Phe, Trp, Ile, Pro etc. Preferred residues are Gly, Ala, Val, Leu and Ile. According to the present invention, the motif C sequence QVH has been preferably replaced by the sequences LVL, LVG, QVL, PIL, QVV, LVA, LAA, LVV, LVI, IVI, III, VVV, QVV, QVA etc., replacement by LVL and LVG being particularly preferred.

In addition to the above mentioned exchange, the polymerase according to the invention can include more mutations, such as deletions, substitutions and/or additions (up to 20 amino acid residues each), provided that the higher extension ratio ($F_{match}/F_{mismatch}$) as compared to the wild type is not adversely affected thereby. The substitutions include, in particular, further (preferably conservative) exchanges in the motif C sequence, which are effected in addition to the above stated replacing of at least one residue in QVH by a lipophilic amino acid residue. Thus, the present invention also includes those DNA polymerases, in particular, which contain an amino acid sequence LVN, LYH, PLQ, LVQ, QDL, QEL, QUV etc. instead of QVH in the C motif.

In addition, it has been found that a DNA polymerase with the sequence QVN instead of QVH in the C motif also has a higher extension ratio ($F_{match}/F_{mismatch}$) as compared to the wild type.

Further, the invention includes Taq polymerase whose QVH sequence has been exchanged as described above. Particularly preferred are those Taq polymerases whose QVH sequence has been replaced by LVL or LVG (based on the Taq polymerase protein sequence shown in SEQ ID NO; 4, the positions 782-784 are affected by the exchange).

In the Klenow fragments according to the invention, it is preferred that at least two amino acid residues in QVH have been replaced by lipophilic amino acid residues. Particularly preferred among the sequences with two exchanges as mentioned above are LVL and LVG, also for the Klenow fragments.

As compared to the mutant QVA known from the literature (Minnick, T. et al., J. Biol. Chem. 274, 3067-3075 (1999)), the polymerase mutants according to the invention have an increased selectivity of primer extension (Example 7, FIG. 5). As shown in FIG. 5, the QVA mutant has an essentially higher tendency to extend mismatches as compared to the LVL mutant according to the invention.

Thus, the amino acid sequence of the DNA polymerases according to the invention has been altered in one or more positions as compared to the wild type DNA polymerases, and this is also reflected on the nucleic acid level. The invention also relates to a DNA sequence which codes for one of the DNA polymerases according to the invention or its Klenow fragment (embodiment (3) of the invention). The invention also relates to a vector which contains the DNA sequence coding for the DNA polymerase (1) or (2), and to a host cell transformed with a vector which contains the DNA sequence coding for the DNA polymerase (1) or (2), and/or which includes a DNA coding for the DNA polymerase (1) or (2). The invention also relates to a process for preparing a DNA polymerase or its Klenow fragment, which comprises culturing the transformed host cell and isolating the DNA polymerase or the Klenow fragment from the culture or the culture supernatant.

Thermostable DNA polymerases according to embodiment (1) or (2) of the invention have a higher selectivity in the polymerase chain reaction (PCR) and discriminate better between individual mismatches and canonic complexes as compared to naturally occurring DNA polymerases. This leads to improved properties of the mutants when used in diagnostic (allele-specific PCR) and molecular-biological (DNA amplification by PCR, cloning) methods. Therefore, the invention also relates to methods in which the DNA polymerase according to the invention or its Klenow fragment can be employed.

The DNA polymerase according to embodiment (1) or (2) of the invention can also be employed in a method for determining the presence or absence of sequence variants in one or more target nucleic acids in an individual sample (embodiment (8)). Such a method preferably comprises one or more of the following steps:
a) adding:
   deoxynucleoside triphosphates;
   one of the DNA polymerases according to the invention;
   at least one discriminating primer containing at least one discriminating nucleotide residue, wherein a primer is added for each sequence variant of a target nucleic acid to be detected, which primer has a sequence complementary to the sequence variant to be detected, and wherein the sequence variant to be detected in the target nucleic acid is complementary to at least one 3'-terminal, 3'-proxi-terminal or 3'-proxi-proxi-terminal nucleotide residue of the discriminating primer;

at least one other primer which is complementary to a primer extension product formed by extension of a discriminating primer;

b) performing a primer extension reaction wherein an extension product of the discriminating primer is obtained substantially only if the sample contains a target nucleic acid with the sequence variant to be detected;

c) separating the product of the primer extension reaction from the template nucleic acid;

d) reiterating steps b) and c) to obtain an amplification product, for example, by polymerase chain reaction;

e) determining the presence or absence of a sequence variant from the presence or absence of the amplification product.

In this connection, the terms used for the description of the method according to the invention have the following meanings:

A "DNA polymerase according to the invention" is a family A DNA polymerase as defined above which includes the A motif with the sequence DYSQIELR (SEQ ID NO:38) in its active site and comprises particular mutations in the C motif. In particular, they also include thermostable DNA polymerases with mutations in the C motif. These mutations are conservative substitutions of the QVH amino acid residues of the C motif and/or the above defined non-conservative substitutions.

A "thermostable DNA polymerase" is a polymerase which is functional even at temperatures of above 42° C. and can be employed, in particular, in PCR-based amplification methods.

In particular, the term "extension reactions" includes reaction mixtures which comprise at least a polymerase, nucleotides, one or more templates and primers. The reaction conditions are selected in such a way that the primer(s) can anneal to the template, and the polymerase catalyzes the extension of the primer(s) by incorporating nucleotides complementary to the template. The product formed is a primer extension product.

A "target nucleic acid" is a nucleic acid segment from a biological sample whose sequence is to be analyzed further by means of the method according to the invention. The biological sample usually consists of genomic DNA. However, the method according to the invention is similarly suitable for analyzing RNA sequence variants. It is not critical whether the sample was isolated from cellular material or from biological fluids, such as blood, serum, plasma, urine or saliva.

A "sequence variant" according to the invention means a target nucleic acid with a particular nucleic acid sequence which exhibits only minute differences from the sequences of other possible target nucleic acids and can be identified by these minute differences. The differences in sequence preferably affect from one to three contiguous nucleotide residues. The present invention is particularly suitable for the identification of sequence variants relating to a single nucleotide residue (SNP). This may be a base exchange, but alternatively, it may also be nucleotide additions or deletions. In this way, different alleles can be distinguished from one another. Point mutations or polymorphisms can also be detected in this way. Thus, in particular, a "sequence variant" also includes point mutations and polymorphisms which are analyzed with respect to prognostic or diagnostic issues.

In a template-directed polymerization of deoxynucleotide triphosphates, a polymerization of the deoxynucleotide triphosphates is effected from the 3' end of a so-called primer, which is hybridized to a single-strand template nucleic acid, to form a sequence complementary to the target nucleic acid. Such polymerization reactions in 5'→3' orientation are preferably performed enzymatically with so-called DNA polymerases, such as Klenow polymerase. Particularly preferred are thermostable DNA polymerases, such as Taq polymerase (Roche Applied Science Catalogue No. 1146165).

A "discriminating primer" within the meaning of the invention is a primer whose sequence is exactly complementary to a particular sequence variant, this sequence having particular differences from another sequence variant which may be present in the sample to be analyzed. In this connection, a "discriminating nucleotide residue" means a nucleotide residue whose complement is formed by different nucleotide residues in the different existing sequence variants.

The "3' terminal nucleotide residue" is the nucleotide residue which is positioned at that terminal end of an oligonucleotide primer which has a free 3'-OH group. The "proxi-terminal nucleotide residue" is the nucleotide residue of an oligonucleotide primer whose end is linked to the 5'-end of the terminal nucleotide residue through a phosphate group. "Proxi-proxi-terminal nucleotide residue" refers to the nucleotide residue whose 3'-end is linked to the 5'-end of the proxi-terminal nucleotide residue through a phosphate group.

As can be seen from the above description of the method according to the invention, the steps a) to e) are essentially an amplification reaction which does or does not result in an amplification product depending on the presence or absence of a particular sequence reaction. Therefore, such methods can be performed according to protocols for PCR reactions known from the prior art.

In this connection, the invention also relates to a kit containing agents for performing the method according to the invention. In particular, such a kit contains a DNA polymerase according to the invention. Optionally, such a kit may contain additional components, such as one or more (discriminating) primers, deoxynucleotide triphosphate, buffers, quantification reagents, especially intercalating reagents, or reagents binding to the minor groove, wherein more preferably reagents from the group consisting of PicoGreen (Molecular Probes), SybrGreen (Molecular Probes), ethidium bromide, Gelstar (Cambrex) and Vista Green (Amersham) are selected, polymerase-blocking antibodies, especially TaqBlock, and agents for the template-directed polymerization of the deoxynucleotide triphosphates. In various embodiments, the individual components of the kit can be alternatively contained either together in one storage container or separately in two or more storage containers.

As can be seen from the Examples stated below, the observable effects in terms of improvement of specificity over the methods available from the prior art can be demonstrated clearly in a quantitative way (cf. Example 7, FIG. 5) and have the result that under PCR amplification conditions, extension products of sequence variant specific primers indeed can be obtained essentially only if the sample to be analyzed contains a target nucleic acid with the sequence variant to be detected.

This specific effect can be optimized by improving and optimizing the respective PCR parameters by means of measures known to the skilled person from the prior art, and adapted to the sequence variant to be respectively detected.

Another embodiment of the present invention relates to the performance of the method according to the invention by means of real time PCR. In this method, the end products of the amplification reaction are not detected by gel electrophoresis, but the course of the amplification reaction is traced by means of suitable fluorescence-labeled hybridization probes, so that kinetic real-time measurements and quantifications are possible.

The hybridization probes to be employed for the methods according to the invention are usually single-stranded nucleic acids, such as single-stranded DNA or RNA or their derivatives, or alternatively, PNAs which hybridize to the target nucleic acid at the annealing temperature of the amplification reaction. Usually, these oligonucleotides have a length of from 20 to 100 nucleotides.

Depending on the precise detection format, the labeling can be introduced at any ribose or phosphate group of the oligonucleotide. Labels at the 5' and 3' end of the nucleic acid molecule are preferred. The type of labeling must be detectable in the real-time mode of the amplification reaction. This is possible, for example, not only with fluorescence labels, but alternatively also by means of labels which are detectable by NMR.

Many different test set-ups are possible. The following three detection format have proven particularly suitable in connection with the present invention:

1. FRET Hybridization Probes:

For this test format, two single-stranded hybridization probes which are complementary to neighboring sites of the same strand of the amplified target nucleic acid are used simultaneously. Both probes have been labeled with different fluorescence components. Upon excitation of a first component with light of a suitable wavelength, it transfers the absorbed energy to the second component according to the principle of fluorescence resonance energy transfer, so that, when both hybridization samples bind to neighboring positions of the target molecule to be detected, a fluorescence emission of the second component can be measured.

Alternatively, a fluorescence-labeled primer and only one labeled oligonucleotide probe can be used (Bernard et al., Analytical Biochemistry 235, 1001-107 (1998)).

2. TaqMan Hybridization Probes:

A single-stranded hybridization probe is labeled with 2 components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'→3' exonuclease activity of the Taq polymerase during the subsequent elongation phase. Thus, the excited fluorescence component and the quencher are separated in space from each other, so that a fluorescence emission of the first component can be measured.

3. Molecular Beacons:

These hybridization probes are also labeled with a first component and a quencher, the labels preferably being positioned at the two ends of the probe. In solution, the two components are in close spatial proximity due to the secondary structure of the probe. After hybridization to the target nucleic acid, both components are separated from one another, so that, after excitation with light of a suitable wavelength, the fluorescence emission of the first component can be measured (Lizardi et al., U.S. Pat. No. 5,118,801).

In alternative embodiments, the respective amplification product can also be detected by a DNA binding dye according to the invention, which upon interaction with a double-stranded nucleic acid emits a corresponding fluorescence signal upon excitation with light of a suitable wavelength. The dyes SybrGreen and SybrGold (Molecular Probes) have proven particularly suitable for this application. Alternatively, intercalating dyes may also be used.

The invention is further illustrated by means of the following Examples and Figures. The procedures described are not to be considered limitations of the invention, but mere examples which, even after modification, still describe the subject matter of the invention.

EXAMPLES

Example 1

Construction of a Library and Purification of Klenow Fragment Variants

The plasmid pQKF$^-$ (Brakman, S., Nieckchen, P., ChemBioChem 2001, 2, 773-7; see also the equivalent plasmid pQE30 shown in SEQ ID NO: 26) enables the expression of the N-terminal 6-his-labeled Klenow fragment of $E.$ $coli$ DNA polymerase I (3'→5' exo$^-$) under the control of a T5 promoter/Double lac operator sequence. The introduction of mutations into the motif C sequence which codes for Q879, V880 and H881 was effected by a two-step megaprimer mutagenesis. PCR reactions were performed by using Pfu-Turbo DNA polymerase (Stratagene) and under standard conditions. The first PCR was performed with a doped primer library (5'-GTA CGT ATG ATC ATG NNN NNN NNN GAT GAA CTG GTA TTT-3'; SEQ ID NO: 5) which was constructed in such a way as to contain 40% non-wild type nucleotides on each of the nine target positions and a 23mer downstream primer (5'-GCT AAT TAA GCT TGG CTG CAG GC-3'; SEQ ID NO: 6), which yielded a 195mer PCR product. The second PCR was performed by using the 195mer purified on agarose gel and a 24mer antisense primer (5'-TAC ATG GAC CTT TAC TTC GAA CGC-3' SEQ ID NO: 7) and yielded a 457 bp product which was digested with Csp45I and HindIII and cloned into pQKF$^-$. The resulting plasmid library was transformed into $E.$ $coli$ XL 1blue (Stratagene), clones were selected from agar plates and separately grown over night in 96-well plates containing Superbroth medium (100 µg/ml ampicillin). Klenow fragment variants were expressed, harvested and lysed in 600 µl cultures using 96-well plates as described. The 300 µl lysates obtained were diluted with 900 µl of storage buffer (50 mM Tris-HCl, pH 7.3, 1 mM DTT, 0.1 mM EDTA, 1 mM PMSF, 1 mM benzamidine, 1 µg/ml leupeptin and 1 µg/ml aprotinin), centrifuged and stored at −80° C.

For primer extension reactions and steady state kinetic measurements, the Klenow fragment and selected mutants were expressed as described above, and purified by means of Ni-NTA agarose (Qiagen) following the manufacturer's instructions, but omitting the imidazole in the lysing and washing steps. The enzymes obtained were >95% pure, which was confirmed by SDS PAGE with Coomassie blue staining. After replacing the buffer (by 100 mM K$_2$HPO$_4$, 1 mM DTT, pH 6.5, with 50% glycerol), concentrations were measured using the nanoOrange assay (Molecular Probes) and adjusted to 1 µg/µl.

Example 2

Screening

The reaction mixtures for screening the library contained 150 nM template, 225 nM primer, 50 mM Tris-HCl, pH 7.3, 10 mM MgCl$_2$, 1 mM DTT, 0.05% Triton® X-100 and 200

μM each of dNTPs. The reactions comprised the 20mer primer FVL20TH (5'-ACA AAA TAC CTG TAT TCC TT-3'; SEQ ID NO: 8) which is designed to bind with its 3'-terminal base to the human SNP G1691A, which is involved in the factor V Leiden mutation. For measurements of pairing extension efficiencies, the 90mer template TFVL90A (5'-GAC ATC ATG AGA GAC ATC GCC TCT GGG CTA ATA GGA CTA CTT CTA ATC TGT AAG AGC AGA TCC CTG GAC AGG CAA GGA ATA CAG GTA TTT-3'; SEQ ID NO: 9) which codes for the mutant allele 1691A of the human factor V-ORF was used, which resulted in a TA base pair at the 3' terminus of the primer. To obtain access to activities of Klenow variants which process a mismatched primer terminus, the 90mer template TFVL90G (5'-GAC ATC ATG AGA GAC ATC GCC TCT GGG CTA ATA GGA CTA CTT CTA ATC TGT AAG AGC AGA TCC CTG GAC AGG CGA GGA ATA CAG GTA TTT-3; SEQ ID NO: 10) which codes for the corresponding wild type allele 1691G was used, which resulted in a TG mismatch at the 3' primer terminus. Both reactions were performed in parallel for each element of the library to enable an evaluation of the activity ratios as extension selectivities. Ten μl of the reaction mixtures was dispensed into black 384-well plates preheated at 37° C. using an automated liquid handling device (Hamilton Microlab Star), followed by adding 5 μl of lysate solution. After 10 min, the reactions were stopped by adding 30 μl of stopping solution (50 mM Tris-HCl, pH 7.3, 100 mM NaCl, 10 mM EDTA) which contained 3.4× SYBRGreen I (Molecular Probes) for quantifying the dsDNA produced by Klenow variants. The fluorescence intensities were quantified by means of a fluorescence plate reader (Polarstar Optima, BMG Labtechnologies GmbH) with excitation at 485 nm and emission at 520 nm. The ratios of the measured fluorescence intensities ($F_{match}/F_{mismatch}$, arbitrary units) were employed for determining the extension selectivity. All DNA polymerases with a higher extension selectivity ratio ($F_{match}/F_{mismatch}$) than that of the wild type were identified as enzymes having an increased extension selectivity.

Example 3

Primer Extension Assays

Primer-template substrates were annealed by mixing 5'-$^{32}$P-labeled primer in a specific reaction buffer (50 mM Tris-HCl, pH 7.3, 10 mM MgCl$_2$, 1 mM DTT, 0.05% Triton® X-100) with a twofold amount of template. The mixture was heated at 95° C. for 5 min and subsequently allowed to cool to room temperature over 1 hour. After the annealing, dNTPs were added, and the solution was incubated at 37° C. for 5 min. 15 μl reactions were initiated by adding 5 μl of enzyme solution in 1× reaction buffer to 10 μl of annealing mixture, followed by incubation at 37° C. for 10 min. The assays included 150 nM primer, 225 nM template, 1 mM each of dNTPs and 590 nM enzyme in a suitable reaction buffer. After 10 min of incubation, the reactions were stopped by adding 30 μl of gel-loading buffer (80% formamide, EDTA, 20 mM), and the product mixtures were analyzed by 14% denaturing PAGE (see FIGS. 1 and 2). The following primer and template sequences were employed in connection with different SNPs (positions underligned):

Human genomic factor V Leiden DNA sequence: Primer: 5'''-ACA AAA TAC CTG TAT TCC TT-3-(SEQ ID NO: 11), wild type template: 5-GAT CCC TGG ACA GGC GAG GAA TAC AGG TAT TTT GT-3 (SEQ ID NO:30), mutant template: 5'-GAT CCC TGG ACA GGC AAG GAA TAC AGG TAT TTT GT-3' (SEQ ID NO:31).

Human somatic BRAF-T1796A mutation: Primer: 5-GAC CCA CTC CAT CGA GAT TTC T-3' (SEQ ID NO: 13), wild type template: 5-GGT CTA GCT ACA GTG AAA TCT CGA TGG AGT GGG TC-3' (SEQ ID NO:32), mutant template: 5-GGT CTA GCT ACA GAG AAA TCT CGA TGG AGT GGG TC-3' (SEQ ID NO:33).

Human dihydropyrimidine dehydrogenase (DpyD) mutation G735A: Primer: 5-GTT TTA GAT GTT AAA TCA CAC TTA T-3' (SEQ ID NO: 15), wild type template: 5'-CTT TCC AGA CAA CGT AAG TGT GAT TTA ACA TCT AAA AC-3' (SEQ ID NO: 34), mutant template: 5'-CTT TCC AGA CAA CAT AAG TGT GAT TTA ACA TCT AAA AC-3' (SEQ ID NO: 35).

Human acid ceramidase mutation A107G: Primer: 5'-CGT TGG TCC TGA AGG AGG AT-3' (SEQ ID NO: 17), wild type template: 5'-AAA TCA ACC TAT CCT CCT TCA GGA CCA ACG TAC-3 (SEQ ID NO: 36), mutant template: 5'-AAA TCA ACC TGT CCT CCT TCA GGA CCA ACG TAC-3' (SEQ ID NO: 37).

Figure 1:
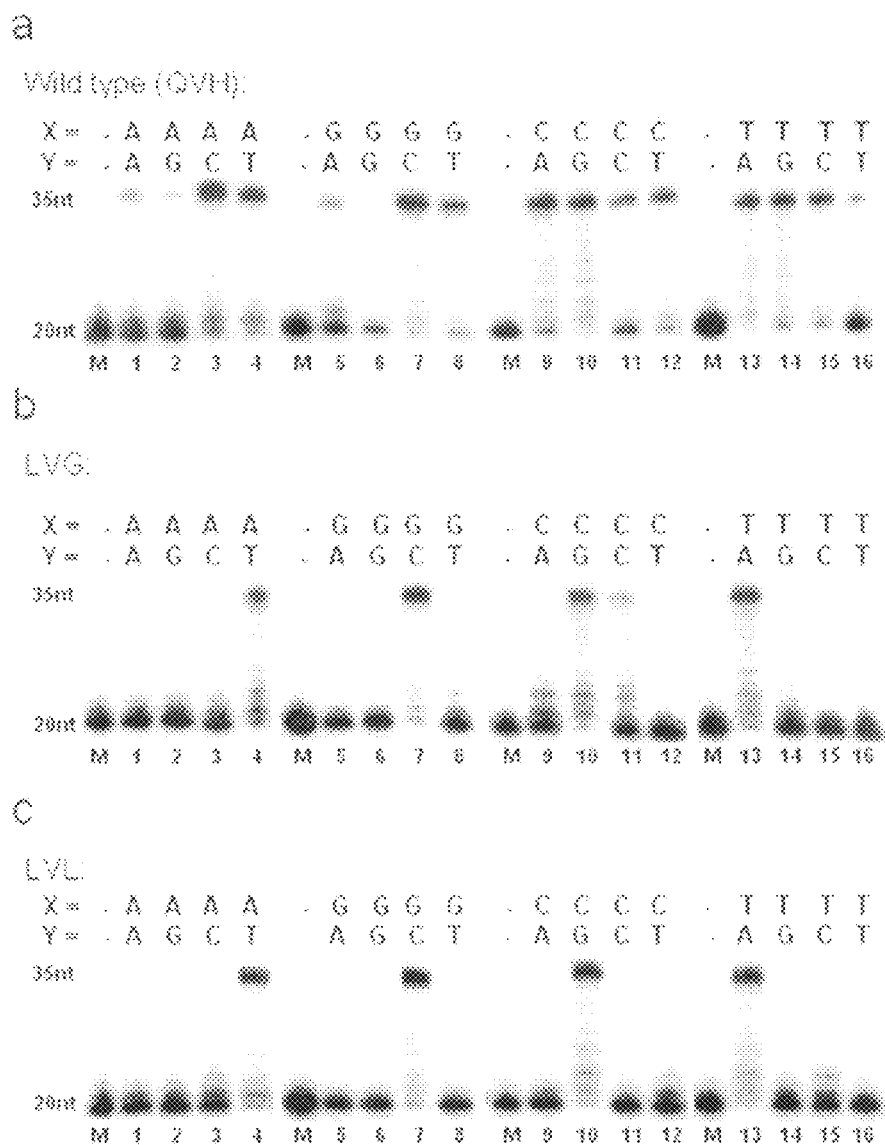
FIG. 1: Autoradiographs after denaturing PAGE for examining the influence of mutations in E. coli DNA polymerase I (Klenow fragment, 5'→3' exonuclease-deficient) in positions 879-881 (SEQ ID NO: 2) on the selectivity of primer extension. Reactions contained 150 nM primer/template complex (primer: 5'-ACA AAA TAC CTG TAT TCC TX-3', X=A, G, C or T (SEQ ID NO: 11); template: 5'-GA TCC CTG GAC AGG CYA GGA ATA CAG GTA TTT TGT-3', Y=A, G, C or T (SEQ ID NO: 12), 1 mM each of dATP, dCTP, TTP, dGTP, and 600 nM DNA polymerase. Incubation at 37° C. for 10 min in buffer (50 mM Tris-HCl, pH 7.3, mM MgCl$_2$, 1 mM DTT, 0.05% Triton® X-100).
Figure 2:
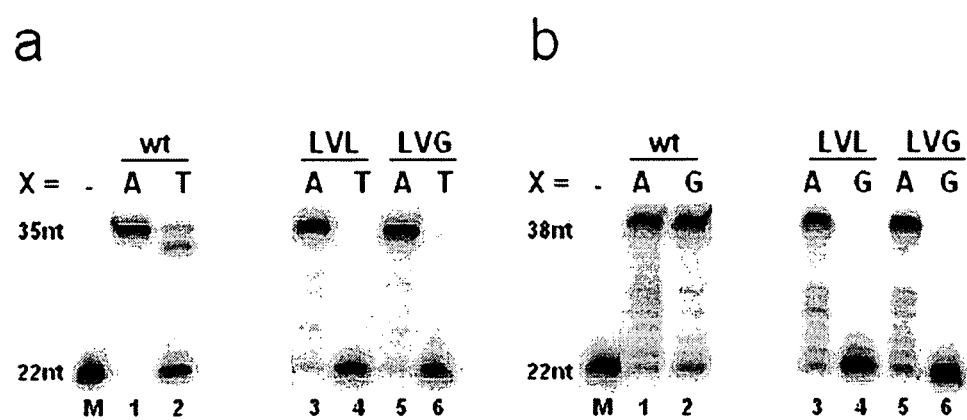
FIG. 2: Autoradiographs after denaturing PAGE for examining the influence of mutations in E. coli DNA polymerase I (Klenow fragment, 5'→3' exonuclease-deficient) in positions 879-881 (based on the Klenow fragment from E. coli as shown in SEQ ID NO: 2) on the selectivity of primer extension. Reactions contained 150 nM primer/template complex [a: primer: 5'-GAC CCA CTC CAT CGA GAT TTC T-3' (SEQ ID NO; 13); templates: 5'-GGT CTA GCT ACA GXG AAA TCT CGA TGG AGT GGG TC-3', X=A or T (SEQ ID NO: 14); b: primer: 5'-GTT TTA GAT GTT AAA TCA CAC TTA T-3' (SEQ ID NO: 15); template: 5-CTT TCC AGA CAA CXT AAG TGT GAT TTA ACA TCT AAA AC-3', X=A or G (SEQ ID NO: 16)], 1 mM each of dATP, dCTP, TTP, dGTP, and 600 nM DNA polymerase. Incubation at 37° C. for 10 min in buffer (50 mM Tris-HCl, pH 7.3, 10 mM MgCl$_2$, 1 mM DTT, 0.05% Triton® X-100).

Thus, the mutations in *E. coli* DNA polymerase I (Klenow fragment, 5'→3'-exonuclease-deficient) with LVL and LVG in positions 879-881 (based on the Klenow fragment from *E. coli* as shown in SEQ ID NO: 2) as compared to the wild type enzyme with QVH in positions 879-881 (FIGS. 1 and 2).

Example 4

Cloning of Taq DNA Polymerase

The plasmid pTTQ18::Taq (SEQ ID NO: 25) was constructed by Engelke et al. (Anal. Biochem. 1990, 191, 396-400 (1990)) and enables the expression of Taq DNA polymerase under the control of a Ptac promoter/lac operator sequence. The LVL mutation was introduced into the Taq QVH motif by PCR using the Stratagene QuikChange® Kit. The resulting mutant plasmid and the wild type plasmid were transformed into *E. coli* XL1 Blue (Stratagene). Clones were selected and grown over night in 20 ml of Superbroth (100 μg/ml carbenicillin). The expression of the Taq clones was performed in cultures in 1l of Superbroth (100 μg/ml carbenicillin), and the cells were harvested after 16 h of induction with 1 mM IPTG. The purification of the Taq DNA polymerases was performed as described by Engelke at al. (Anal. Biochem. 1990, 191, 396-400). Instead of purification by ion-exchange, gel filtration using a column with Sephadex® 75 (Amersham) was applied. The enzymes obtained were >90% pure, which was confirmed by SDS PAGE with Coomassie blue staining. The concentrations were measured using the nanoOrange assay (Molecular Probes) and SDS PAGE with Coomassie blue staining.

Example 5

Primer Extension with Catalysis by Taq DNA Polymerase

Figure 3:
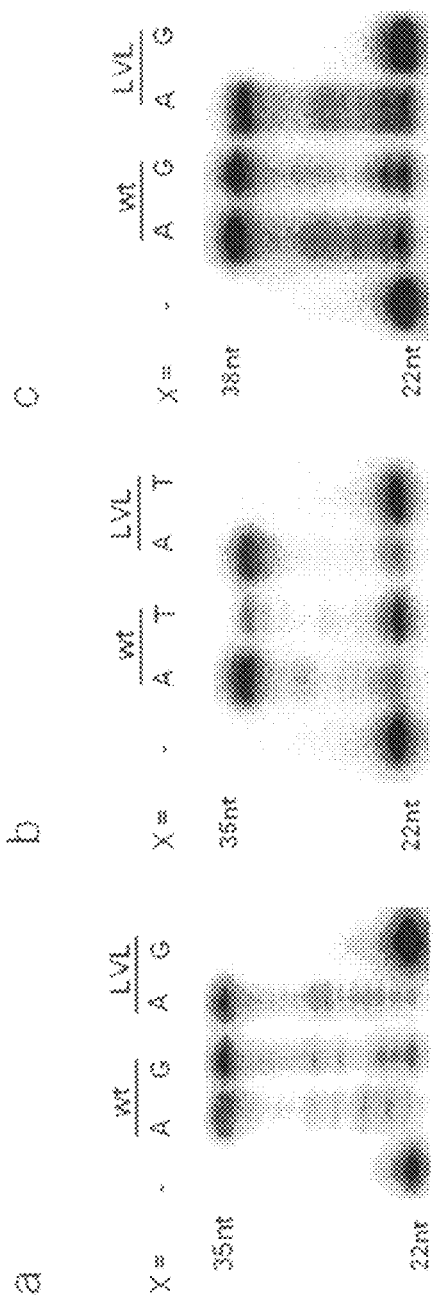
FIG. 3: Autoradiographs after denaturing PAGE for examining the influence of mutations in the QVH motif in Taq DNA polymerase I on the selectivity of primer extension. Reactions contained 150 nM primer/template complex [a: primer: 5'-ACA AAA TAC CTG TAT TCC TX-3', X=T (SEQ ID NO: 11); template: 5'-GA TCC CTG GAC AGG CYA GGA ATA CAG GTA TTT TGT-3'Y=A or G (SEQ ID NO: 12); b: primer: 5'-GAC CCA CTC CAT CGA GAT TTC T-3' (SEQ ID NO: 13); template: 5'-GGT CTA GCT ACA GXG AAA TCT CGA TGG AGT GGG TC-3', X=A or T (SEQ ID NO: 14); c: primer: 5'-GTT TTA GAT GTT AAA TCA CAC TTA T-3' (SEQ ID NO: 15); template: 5'-CTT TCC AGA CAA CXT AAG TGT GAT TTA ACA TCT AAA AC-3', X=A or G (SEQ ID NO: 16)], 1 mM each of dATP, dCTP, dGTP, and 0.6 ng of DNA polymerase. Incubation at 37° C. for 10 min in buffer (50 mM Tris-HCl (pH 9.2 at 25° C.), 16 mM ammonium sulfate, 2.5 mM MgCl$_2$, 0.1% Tween® 20).

Primer-template substrates were annealed by mixing 5'-$^{32}$P-labeled primer in specific reaction buffer (50 mM Tris-HCl, pH 9.2 at 25° C., 16 mM ammonium sulfate and 2.5 mM MgCl$_2$, 0.1% Tween® 20) with a twofold amount of template. The mixture was heated at 95° C. for 10 min and subsequently allowed to cool to room temperature over 1 hour. After the annealing, dNTPs were added, and the solution was incubated at 37° C. for 5 min. 15 μl reactions were initiated by adding 5 μl of enzyme solution in 1× reaction buffer to 10 μl of annealing mixture, followed by incubation at 72° C. for 10 min. The assays included 150 nM primer, 225 nM template, 1 mM each of dNTPs and 0.5 ng of Taq LVL DNA polymerase (mutant polymerase) and 0.06 ng of Taq DNA polymerase in a suitable reaction buffer. After 10 min of incubation, the reactions were stopped by adding 30 µl of gel-loading buffer (80% formamide, EDTA, 20 mM), and the product mixtures were analyzed by 14% denaturing PAGE (see FIG. 3). As to the primer and template sequences used in connection with the SNPs human genomic factor V Leiden DNA sequence, human somatic BRAF-T1796A mutation and human dihydropyrimidine dehydrogenase (DPyD) mutation G735A, reference is made to Example 3.

Example 6

Real-Time PCR Experiments

Figure 4:
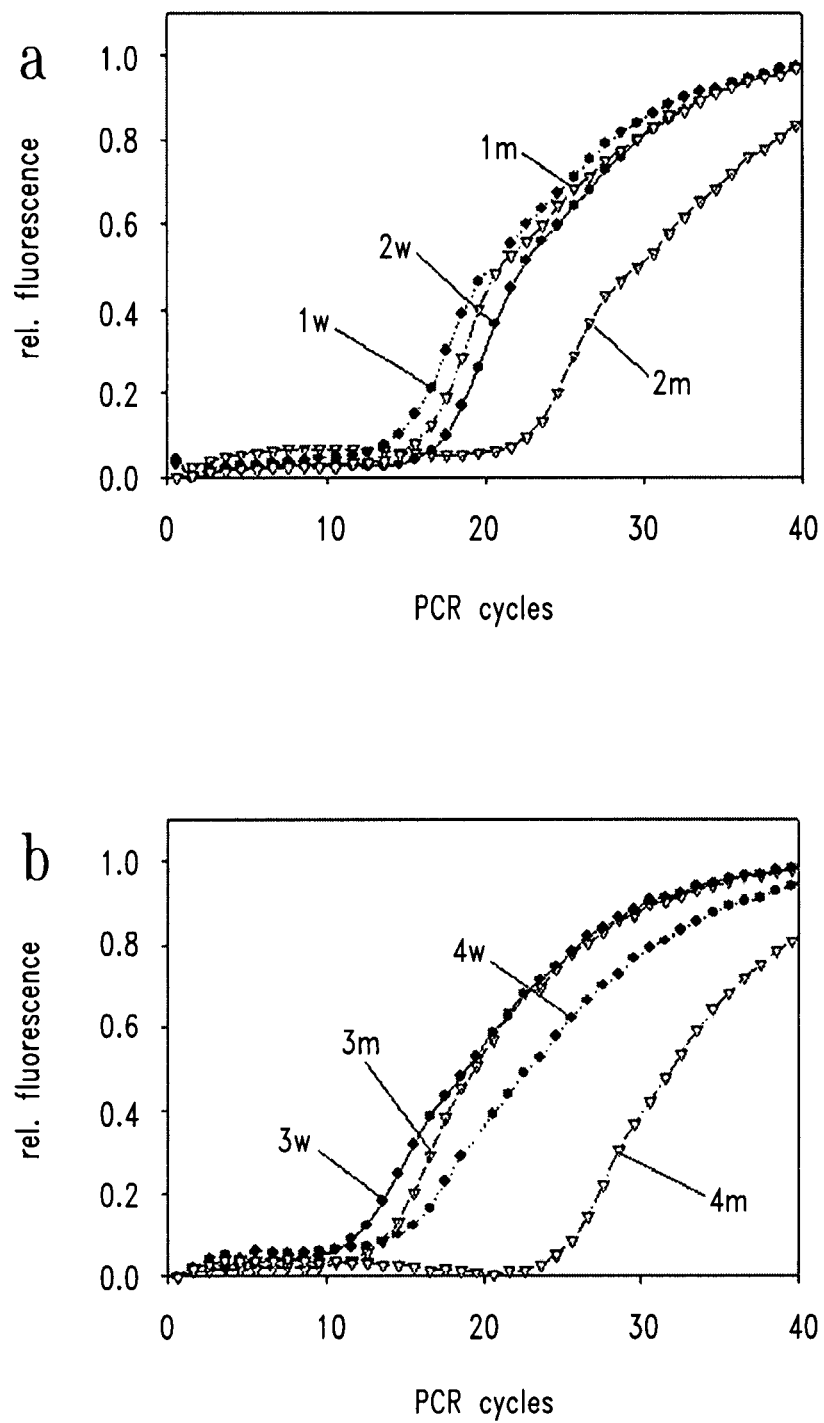
FIG. 4: Real time PCR experiments with Taq (wt) (SEQ ID NO: 4) and LVL mutant (SEQ ID NO: 4 with LVL in positions 782-784). The experiments were performed by means of an iCycler (BIORAD) system. A typical reaction in 20 μl contained: 40 pM of the respective template in Taq DNA polymerase buffer (50 mM Tris-HCl (pH 9.2 at 25° C.), 16 mM ammonium sulfate, 2.5 mM MgCl$_2$, 0.1% Tween® 20, 0.3 mM dNTPs), 0.5 μM of the two primers and 95 ng of Taq DNA polymerase, and 1/50,000 of SybrGreen I 10,000× solution in DMSO (Molecular Probes). The PCR was performed with the following program: cycles at 95° C. for 30 s, 55° C. for 35 s, and 72° C. for 40 s. Reactions 1w, 2w, 3w and 4w were performed with the wild type enzyme, while 1m, 2m, 3m and 4m were performed with the LVL mutant. DNA sequences.

Real-time PCR was performed using an iCycler system (BIORAD). The reactions were performed in a total volume of 20 µl which contained 4 pM of the respective templates in Taq DNA polymerase buffer (50 mM Tris-HCl, pH 9.2 at 25° C., 16 mM ammonium sulfate and 2.5 mM MgCl$_2$, 0.1% Tween® 20. The final mixtures contained dNTPs (200 µM each of dATP, dGTP, dCTP and TTP), primers (0.5 µM each of the respective primer probe and the reverse primer) and 13 ng of Taq DNA polymerase (SEQ ID NO: 4), 95 ng of DNA polymerase from Taq LVL mutant (SEQ ID NO: 4 with LVL in positions 782-784) and an aqueous 1/50,000 dilution of a 10,000 fold solution of SybrGreen I in DMSO (Molecular Probes). All PCR amplifications were performed using the following program: Initial denaturing at 95° C. for 3 min, followed by 40 cycles of denaturing at 95° C. for 30 s, primer annealing at 55° C. for 35 s and extension at 72° C. for 40 s. The results presented are derived from independent triplicate measurements repeated at least three times and issued from a parent mixture. The results are summarized in FIG. 4. The following DNA sequences were employed:

Sequences in connection with BRAF: Primer probe BrafT: 5'-d(GAC CCA CTC CAT CGA GAT TTC T) (SEQ ID NO: 19), reverse primer: 5'-d(AGA GGA AAG ATG AAG TAC TAT G) (SEQ ID NO: 20), target template BrafX: 5'-d(CAA CTG TTC AAA CTG ATG GGA CCC ACT CCA TCG AGA TTT CXC TGT AGC TAG ACC AAA ATC ACC TAT TTT TAC TGT GAG GTC TIC ATG MG MA TAT ATC TGA GGT GTA GTA AGT AAA GGA AAA CAG TAG ATC TCA TTT TCC TAT CAG AGC AAG CAT TAT GM GAG TTT AGG TAA GAG ATC TAA TTT CTA TAA TTC TGT AAT ATA ATA TTC TTT AAA ACA TAG TAC TTC ATC TTT CCT CT), X=A, BrafA, X=T, BrafT (SEQ ID NO: 21). Sequences in connection with DPyD: Primer probe DpyDT: 5'-d(GTT TTA GAT GT TAA ATC ACA CTT AT) (SEQ ID NO: 22), reverse primer: (5'-d(AAA GCT CCT TTC TGA ATA TTG AG) (SEQ ID NO: 23), target template DPyDX: 5'-d(AAA ATG TGA GAA GGG ACC TCA TAA AAT ATG TCA TAT GGA AAT GAG CAG ATA ATA AAG ATT ATA GCT TTT CTT TGT CAA ATG GAG ACT CAA TAT CTT TAC TCT TTC ATC AGG ACA TTG TGA CAA ATG TTT CCC CCA GAA TCA TCC GGG GM CCA CCT CTG GCC CCA TGT ATG GCC CTG GAC AAA GCT CCT TTC TGA ATA TTG AGC TCA TCA GTG AGA AAA CGG CTG CAT ATT GGT GTC AAA GTG TCA CTG MC TAA AGG CTG ACT TTC CAG ACA ACX TAA GTG TGA TTT AAC ATC TAA AAC), X=A DpyDA, X=T, DpyDG (SEQ ID NO: 24). The oligonucleotides BrafX and DpyDX (SEQ ID NOS: 21 and 24) were synthesized and purified by IBA, Göttingen, Germany.

Example 7 (Comparative Example)

Comparison of Mismatch Discrimination

A mutant according to the invention and a mutant known from the literature of *E. coli* DNA polymerase I (Klenow fragment, 5'→3'-exonuclease-deficient) in positions 879-881 (SEQ ID NO: 2) were compared for their selectivity of primer extension. The mutants employed were the LVL mutant (SEQ ID NO: 2 with LVL in positions 879-881) and the QVA mutant which corresponds to the Klenow fragment with H881A from Minnick, T. et al., J. Biol. Chem. 274, 3067-3075 (1999) (SEQ ID NO: 2 with HVA in positions 879-881).

With the two mutants mentioned, primer extension assays according to Example 3 were performed. The mismatch discrimination with the human genomic factor V Leiden DNA sequence was tested: Primer: 5'-ACA AAA TAC CTG TAT TCC TT-3' (SEQ ID NO: 11), wild type template: 5'-GAT CCC TGG ACA GGC GAG GAA TAC AGG TAT TTT GT-3' (SEQ ID NO: 30), mutant template: 5'-GAT CCC TGG ACA GGC AAG GAA TAC AGG TAT TTT GT-3' (SEQ ID NO: 31). The tendencies of the two mutants to extend mismatches as compared to canonic complexes were compared. As shown in FIG. 5, the QVA mutant has a substantially higher tendency to extend mismatches as compared to the LVL mutant.

The invention claimed is:

1. A family A DNA polymerase or its Klenow fragment comprising:
   the A motif with the sequence DYSQIELR (SEQ ID NO:38), and
   (ii) a modified motif C sequence wherein at least the amino acid residue Q879 in the wild type motif C sequence QVH in positions 879-881 of the *E. coli* DNA polymerase Klenow fragment shown in SEQ ID NO: 2 has been replaced by a lipophilic amino acid residue,
   wherein the DNA polymerase or its Klenow fragment has an enhanced mismatch discrimination activity as compared to the corresponding wild type polymerase or its Klenow fragment.

2. The DNA polymerase or its Klenow fragment according to claim 1, wherein the DNA polymerase is a bacterial DNA polymerase.

3. A DNA sequence which encodes for a DNA polymerase or its Klenow fragment according to claim 1.

4. A vector comprising the DNA sequence according to claim 3.

5. A host cell which has been transformed with the vector according to claim 4.

6. A method for the preparation of a DNA polymerase or its Klenow fragment, comprising culturing a host cell according to claim 5 and isolating the DNA polymerase or its Klenow fragment from the culture or the culture supernatant.

7. A kit for determining the presence or absence of at least one sequence variant in one or more target nucleic acids in an individual sample, comprising at least one DNA polymerase according to claim 1.

8. The kit according to claim 7, additionally containing one or more of the following components:
   one or more discriminating primers containing at least one discriminating nucleotide residue, wherein the sequence variant to be detected in the target nucleic acid is complementary to at least one 3'-terminal, 3'-proxi-terminal or 3'-proxi-proxi-terminal nucleotide residue of the discriminating primer;
   one or more other primers which are complementary to a primer extension product formed by extension of said discriminating primers;
   deoxynucleoside triphosphates;
   buffers;
   quantification reagents; and
   polymerase-blocking antibodies.

9. The DNA polymerase or its Klenow fragment according to claim 2, wherein the DNA polymerase is a thermostable DNA polymerase.

10. The DNA polymerase or its Klenow fragment according to claim 9, wherein the DNA polymerase is a polymerase selected from the group consisting of polymerases from *E. coli, Aquifex, Borrelia, Bacillus, Chlamydia, Chlamydophila, Chloroflexus, Haemophilus, Heliobacter, Lactococcus, Methylobacterium, Mycobacterium, Rhodothermus, Rickettsia, Streptococcus, Streptomyces, Synechocystis, Treponema, Thermus aquaticus, Thermus thermophilus, Thermus filiformis, Rhodothermus obamensis* and *Bacillus stearothermophilus*.

11. The DNA polymerase or its Klenow fragment according to claim 1, wherein said lipophilic amino acid residue is selected from the group of residues consisting of Gly, Ala, Val, Leu, Ile, Pro, Phe, Met and Trp.

12. The DNA polymerase or its Klenow fragment according to claim 11, wherein said lipophilic amino acid residue is selected from the group of residues consisting of Gly, Ala, Val, Leu, and Ile.

13. The DNA polymerase or its Klenow fragment according to claim 1, wherein in the modified motif C sequence, H881 in the wild type motif C sequence QVH in positions 879-881 has been further replaced by a lipophilic amino acid residue.

14. The DNA polymerase or its Klenow fragment according to claim 13, wherein said lipophilic amino acid residue is selected from the group of residues consisting of Gly, Ala, Val, Leu, Ile, Pro, Phe, Met and Trp.

15. The DNA polymerase or its Klenow fragment according to claim 14, wherein said lipophilic amino acid residue is selected from the group of residues consisting of Gly, Ala, Val, Leu and Ile.

16. The DNA polymerase or its Klenow fragment according to claim 1, wherein the amino acid residue in position 880 of the modified motif C sequence is selected from the group of residues consisting of Val, Leu, Ile, Ala and Tyr.

17. The DNA polymerase or its Klenow fragment according to claim 16, wherein the amino acid residue in position 880 is selected from the group of residues consisting of Val and Ile.

18. The DNA polymerase or its Klenow fragment according to claim 1, wherein in the modified motif C, the wild type motif C sequence QVH has been replaced by a sequence selected from the group consisting of LVL and LVG.

19. The DNA polymerase or its Klenow fragment according to claim 1, wherein the DNA polymerase is a modified Taq polymerase in which the sequence QVH in positions 782-784 of a wild type Taq polymerase shown in SEQ ID NO:4 has been replaced by a sequence selected from the group consisting of LVL and LVG.

20. The DNA polymerase or its Klenow fragment according to claim 1, wherein the Klenow fragment is a modified Klenow fragment in which the sequence QVH in positions 879-881 of a wild type Klenow fragment shown in SEQ ID NO:2 has been replaced by a sequence selected from the group consisting of LVL and LVG.

21. A method for performing a nucleic acid extension reaction, comprising extending a DNA primer in the presence of the DNA polymerase or its Klenow fragment of claim 1.

22. The method of claim 21 wherein the nucleic acid extension reaction is selected from the group consisting of allele-specific PCR, DNA amplification by means of PCR, and cloning.

23. The method of claim 21, wherein the method is suitable for determining the presence or absence of at least one sequence variant in one or more target nucleic acids in an individual sample.

24. The method according to claim 23 including the following steps:
   a) adding:
      deoxynucleoside triphosphates;
      a DNA polymerase according to claim 1;
      at least one discriminating primer containing at least one discriminating nucleotide residue, wherein a primer is added for each sequence variant to be detected of a target nucleic acid, which primer has a sequence complementary to the sequence variant to be detected, and wherein the sequence variant to be detected in the target nucleic acid is complementary to at least one 3'-terminal, 3'-proxi-terminal or 3'-proxi-proxi-terminal nucleotide residue of the discriminating primer;
      at least one other primer which is complementary to a primer extension product formed by extension of the discriminating primer;

b) performing a primer extension reaction wherein an extension product of the discriminating primer is obtained substantially only if the sample contains a target nucleic acid with the sequence variant to be detected;

c) separating the extension product of the primer extension reaction from its template nucleic acid;

d) reiterating steps b) and c) to obtain an amplification product; and e) determining the presence or absence of a sequence variant from the presence or absence of the amplification product.

25. The method according to claim 24, wherein steps b) to e) are performed as real-time PCR or real-time RT-PCR.

26. The kit of claim 8, wherein the quantification reagents are selected from the group consisting of intercalating reagents and reagents binding to the minor groove of a double-stranded DNA molecule.

27. The kit of claim 8, wherein the polymerase-blocking antibody is TaqBlock.

* * * * *

SEQUENCE LISTING

<160> NUMBER OF SEQ ID NOS: 38

<210> SEQ ID NO 1
<211> LENGTH: 2787
<212> TYPE: DNA
<213> ORGANISM: Artificial Sequence
<220> FEATURE:
<223> OTHER INFORMATION: E. Coli wild type Klenow fragment of DNA
      polymerase I

<400> SEQUENCE: 1

```
atggttcaga tcccccaaaa tccacttatc cttgtagatg gttcatctta tctttatcgc      60
gcatatcacg cgtttccccc gctgactaac agcgcaggcg agccgaccgg tgcgatgtat     120
ggtgtcctca acatgctgcg cagtctgatc atgcaatata aaccgacgca tgcagcggtg     180
gtctttgacg ccaagggaaa aacctttcgt gatgaactgt ttgaacatta caaatcacat     240
cgcccgccaa tgccggacga tctgcgtgca caaatcgaac ccttgcacgc gatggttaaa     300
```

```
gcgatgggac tgccgctgct ggcggtttct ggcgtagaag cggacgacgt tatcggtact    360
ctggcgcgcg aagccgaaaa agccgggcgt ccggtgctga tcagcactgg cgataaagat    420
atggcgcagc tggtgacgcc aaatattacg cttatcaata ccatgacgaa taccatcctc    480
ggaccggaag aggtggtgaa taagtacggc gtgccgccag aactgatcat cgatttcctg    540
gcgctgatgg gtgactcctc tgataacatt cctggcgtac cgggcgtcgg tgaaaaaacc    600
gcgcaggcat tgctgcaagg tcttggcgga ctggatacgc tgtatgccga gccagaaaaa    660
attgctgggt tgagcttccg tggcgcgaaa acaatggcag cgaagctcga gcaaaacaaa    720
gaagttgctt atctctcata ccagctggcg acgattaaaa ccgacgttga actggagctg    780
acctgtgaac aactggaagt gcagcaaccg gcagcggaag agttgttggg gctgttcaaa    840
aagtatgagt tcaaacgctg gactgctgat gtcgaagcgg gcaaatggtt acaggccaaa    900
ggggcaaaac cagccgcgaa gccacaggaa accagtgttg cagacgaagc accagaagtg    960
acggcaacgg tgatttctta tgacaactac gtcaccatcc ttgatgaaga aacactgaaa   1020
gcgtggattg cgaagctgga aaaagcgccg gtatttgcat ttgataccga aaccgacagc   1080
cttgataaca tctctgctaa cctggtcggg ctttcttttg ctatcgagcc aggcgtagcg   1140
gcatatattc cggttgctca tgattatctt gatgcgcccg atcaaatctc tcgcgagcgt   1200
gcactcgagt tgctaaaacc gctgctgaaa gatgaaaagg cgctgaaggt cgggcaaaac   1260
ctgaaatacg atcgcggtat tctggcgaac tacggcattg aactgcgtgg gattgcgttt   1320
gataccatgc tggagtccta cattctcaat agcgttgccg ggcgtcacga tatggacagc   1380
ctcgcggaac gttggttgaa gcacaaaacc atcacttttg aagagattgc tggtaaaggc   1440
aaaaatcaac tgacctttaa ccagattgcc ctcgaagaag ccggacgtta cgccgccgaa   1500
gatgcagatg tcaccttgca gttgcatctg aaaatgtggc cggatctgca aaaacacaaa   1560
gggccgttga acgtcttcga gaatatcgaa atgccgctgg tgccggtgct ttcacgcatt   1620
gaacgtaacg gtgtgaagat cgatccgaaa gtgctgcaca atcattctga agagctcacc   1680
cttcgtctgg ctgagctgga aaagaaagcg catgaaattg caggtgagga atttaacctt   1740
tcttccacca agcagttaca aaccattctc tttgaaaaac agggcattaa accgctgaag   1800
aaaacgccgg gtggcgcgcc gtcaacgtcg gaagaggtac tggaagaact ggcgctggac   1860
tatccgttgc caaaagtgat tctggagtat cgtggtctgg cgaagctgaa atcgacctac   1920
accgacaagc tgccgctgat gatcaacccg aaaaccgggc gtgtgcatac ctcttatcac   1980
caggcagtaa ctgcaacggg acgtttatcg tcaaccgatc ctaacctgca aaacattccg   2040
gtgcgtaacg aagaaggtcg tcgtatccgc caggcgttta ttgcgccaga ggattatgtg   2100
attgtctcag cggactactc gcagattgaa ctgcgcatta tggcgcatct ttcgcgtgac   2160
aaaggcttgc tgaccgcatt cgcggaagga aaagatatcc accgggcaac ggcggcagaa   2220
gtgtttggtt tgccactgga aaccgtcacc agcgagcaac gccgtagcgc gaaagcgatc   2280
aactttggtc tgatttatgg catgagtgct ttcggtctgg cgcggcaatt gaacattcca   2340
cgtaaagaag cgcagaagta catggaccct tacttcgaac gctaccctgg cgtgctggag   2400
tatatgaacg caccggtgcc tcaggcgaaa gagcagggct acgttgaaac gctggacgga   2460
cgccgtctgt atctgccgga tatcaaatcc agcaatggtg ctcgtcgtgc agcggctgaa   2520
cgtgcagcca ttaacgcgcc aatgcaggga accgccgccg acattatcaa acgggcgatg   2580
attgccgttg atgcgtggtt acaggctgag caaccgcgtg tacgtatgat catgcaggta   2640
```

```
cacgatgaac tggtatttga agttcataaa gatgatgttg atgccgtcgc gaagcagatt    2700
catcaactga tggaaaactg tacccgtctg gatgtgccgt tgctggtgga agtggggagt    2760
ggcgaaaact gggatcaggc gcactaa                                        2787

<210> SEQ ID NO 2
<211> LENGTH: 928
<212> TYPE: PRT
<213> ORGANISM: Artificial Sequence
<220> FEATURE:
<223> OTHER INFORMATION: E.coli Klenow fragment of DNA polymerase I

<400> SEQUENCE: 2

Met Val Gln Ile Pro Gln Asn Pro Leu Ile Leu Val Asp Gly Ser Ser
 1               5                  10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
            100                 105                 110

Glu Ala Asp Asp Val Ile Gly Thr Leu Ala Arg Glu Ala Glu Lys Ala
        115                 120                 125

Gly Arg Pro Val Leu Ile Ser Thr Gly Asp Lys Asp Met Ala Gln Leu
    130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
    210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
        275                 280                 285

Ala Asp Val Glu Ala Gly Lys Trp Leu Gln Ala Lys Gly Ala Lys Pro
    290                 295                 300

Ala Ala Lys Pro Gln Glu Thr Ser Val Ala Asp Glu Ala Pro Glu Val
305                 310                 315                 320

Thr Ala Thr Val Ile Ser Tyr Asp Asn Tyr Val Thr Ile Leu Asp Glu
                325                 330                 335
```

-continued

Glu Thr Leu Lys Ala Trp Ile Ala Lys Leu Glu Lys Ala Pro Val Phe
            340                 345                 350

Ala Phe Asp Thr Glu Thr Asp Ser Leu Asp Asn Ile Ser Ala Asn Leu
            355                 360                 365

Val Gly Leu Ser Phe Ala Ile Glu Pro Gly Val Ala Ala Tyr Ile Pro
            370                 375                 380

Val Ala His Asp Tyr Leu Asp Ala Pro Asp Gln Ile Ser Arg Glu Arg
385                 390                 395                 400

Ala Leu Glu Leu Leu Lys Pro Leu Leu Glu Asp Glu Lys Ala Leu Lys
            405                 410                 415

Val Gly Gln Asn Leu Lys Tyr Asp Arg Gly Ile Leu Ala Asn Tyr Gly
            420                 425                 430

Ile Glu Leu Arg Gly Ile Ala Phe Asp Thr Met Leu Glu Ser Tyr Ile
            435                 440                 445

Leu Asn Ser Val Ala Gly Arg His Asp Met Asp Ser Leu Ala Glu Arg
            450                 455                 460

Trp Leu Lys His Lys Thr Ile Thr Phe Glu Glu Ile Ala Gly Lys Gly
465                 470                 475                 480

Lys Asn Gln Leu Thr Phe Asn Gln Ile Ala Leu Glu Glu Ala Gly Arg
            485                 490                 495

Tyr Ala Ala Glu Asp Ala Asp Val Thr Leu Gln Leu His Leu Lys Met
            500                 505                 510

Trp Pro Asp Leu Gln Lys His Lys Gly Pro Leu Asn Val Phe Glu Asn
            515                 520                 525

Ile Glu Met Pro Leu Val Pro Val Leu Ser Arg Ile Glu Arg Asn Gly
            530                 535                 540

Val Lys Ile Asp Pro Lys Val Leu His Asn His Ser Glu Glu Leu Thr
545                 550                 555                 560

Leu Arg Leu Ala Glu Leu Glu Lys Lys Ala His Glu Ile Ala Gly Glu
            565                 570                 575

Glu Phe Asn Leu Ser Ser Thr Lys Gln Leu Gln Thr Ile Leu Phe Glu
            580                 585                 590

Lys Gln Gly Ile Lys Pro Leu Lys Lys Thr Pro Gly Gly Ala Pro Ser
            595                 600                 605

Thr Ser Glu Glu Val Leu Glu Glu Leu Ala Leu Asp Tyr Pro Leu Pro
            610                 615                 620

Lys Val Ile Leu Glu Tyr Arg Gly Leu Ala Lys Leu Lys Ser Thr Tyr
625                 630                 635                 640

Thr Asp Lys Leu Pro Leu Met Ile Asn Pro Lys Thr Gly Arg Val His
            645                 650                 655

Thr Ser Tyr His Gln Ala Val Thr Ala Thr Gly Arg Leu Ser Ser Thr
            660                 665                 670

Asp Pro Asn Leu Gln Asn Ile Pro Val Arg Asn Glu Glu Gly Arg Arg
            675                 680                 685

Ile Arg Gln Ala Phe Ile Ala Pro Glu Asp Tyr Val Ile Val Ser Ala
            690                 695                 700

Asp Tyr Ser Gln Ile Glu Leu Arg Ile Met Ala His Leu Ser Arg Asp
705                 710                 715                 720

Lys Gly Leu Leu Thr Ala Phe Ala Glu Gly Lys Asp Ile His Arg Ala
            725                 730                 735

Thr Ala Ala Glu Val Phe Gly Leu Pro Leu Glu Thr Val Thr Ser Glu
            740                 745                 750

Gln Arg Arg Ser Ala Lys Ala Ile Asn Phe Gly Leu Ile Tyr Gly Met

```
              755                 760                 765
Ser Ala Phe Gly Leu Ala Arg Gln Leu Asn Ile Pro Arg Lys Glu Ala
         770                 775                 780

Gln Lys Tyr Met Asp Leu Tyr Phe Glu Arg Tyr Pro Gly Val Leu Glu
785                 790                 795                 800

Tyr Met Glu Arg Thr Arg Ala Gln Ala Lys Glu Gln Gly Tyr Val Glu
                 805                 810                 815

Thr Leu Asp Gly Arg Arg Leu Tyr Leu Pro Asp Ile Lys Ser Ser Asn
             820                 825                 830

Gly Ala Arg Arg Ala Ala Glu Arg Ala Ala Ile Asn Ala Pro Met
         835                 840                 845

Gln Gly Thr Ala Ala Asp Ile Ile Lys Arg Ala Met Ile Ala Val Asp
     850                 855                 860

Ala Trp Leu Gln Ala Glu Gln Pro Arg Val Arg Met Ile Met Gln Val
865                 870                 875                 880

His Asp Glu Leu Val Phe Glu Val His Lys Asp Asp Val Asp Ala Val
                 885                 890                 895

Ala Lys Gln Ile His Gln Leu Met Glu Asn Cys Thr Arg Leu Asp Val
             900                 905                 910

Pro Leu Leu Val Glu Val Gly Ser Gly Glu Asn Trp Asp Gln Ala His
         915                 920                 925
```

<210> SEQ ID NO 3
<211> LENGTH: 2499
<212> TYPE: DNA
<213> ORGANISM: Artificial Sequence
<220> FEATURE:
<223> OTHER INFORMATION: Wildtype Taq polymerase

<400> SEQUENCE: 3

```
atgagggga tgctgcccct ctttgagccc aagggccggg tcctcctggt ggacggccac    60
cacctggcct accgcacctt ccacgccctg aagggcctca ccaccagccg ggggagccg   120
gtgcaggcgg tctacggctt cgccaagagc ctcctcaagg ccctcaagga ggacgggga   180
gcggtgatcg tggtctttga cgccaaggcc cctccttcc gccacgaggc ctacggggg   240
tacaaggcgg ccgggcccc cacgccggag actttcccc ggcaactcgc cctcatcaag   300
gagctggtgg acctcctggg gctggcgcgc ctcgaggtcc cgggctacga ggcggacgac   360
gtcctggcca gctggccaa gaaggcggaa aaggagggct acgaggtccg catcctcacc   420
gccgacaaag ccttttacca gctcctttcc gaccgcatcc acgtcctcca ccccgagggg   480
tacctcatca cccccggcctg gctttgggaa aagtacggcc tgaggcccga ccagtgggcc   540
gactaccggg ccctgaccgg ggacgagtcc gacaaccttc cggggtcaa gggcatcggg   600
gagaagacgg cgaggaagct tctggaggag tgggggagcc tggaagccct cctcaagaac   660
ctggaccggc tgaagcccgc catccggag aagatcctgg cccacatgga cgatctgaag   720
ctctcctggg acctggccaa ggtgcgcacc gacctgcccc tggaggtgga cttcgccaaa   780
aggcgggagc ccgaccggga gaggcttagg gcctttctgg agaggcttga gtttggcagc   840
ctcctccacg agttcggcct tctggaaagc cccaaggccc tggaggaggc ccctggcc   900
ccgccggaag gggccttcgt gggctttgtg cttttcccgca aggagcccat gtgggccgat   960
cttctggccc tggccgccgc cagggggggc cgggtccacc gggcccccga gccttataaa  1020
gccctcaggg acctgaagga ggcgcggggg cttctcgcca aagacctgag cgttctggcc  1080
ctgagggaag gccttggcct cccgcccggc gacgacccca tgctcctcgc ctacctcctg  1140
```

```
gaccettteca acaccacccc cgagggggtg gcccggcgct acggcgggga gtggacggag    1200
gaggcggggg agcgggccgc cctttccgag aggctcttcg ccaacctgtg ggggaggctt    1260 gaggggagg agaggctcct ttggctttac cgggaggtgg agaggcccct ttccgctgtc    1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga cccettgccg gacctcatcc accccaggac gggccgcctc    1680
cacacccgct tcaaccagac ggccacggcc acgggcaggc taagtagctc cgatcccaac    1740
ctccagaaca tccccgtccg caccccgctt gggcagagga tccgccgggc cttcatcgcc    1800
gaggaggggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccct gatgcgccgg    1980 gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg    2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag    2460
gtggggatag ggaggactg gctctccgcc aaggagtga                            2499
```

<210> SEQ ID NO 4
<211> LENGTH: 832
<212> TYPE: PRT
<213> ORGANISM: Artificial Sequence
<220> FEATURE:
<223> OTHER INFORMATION: Wildtype Taq polymerase

<400> SEQUENCE: 4

```
Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
```

-continued

```
            115                 120                 125
Ala Glu Lys Glu Gly Tyr Glu Val Arg Ile Leu Thr Ala Asp Lys Asp
            130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
        210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
        530                 535                 540
```

```
Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 5
<211> LENGTH: 39
<212> TYPE: DNA
<213> ORGANISM: Artificial Sequence
<220> FEATURE:
<221> NAME/KEY: misc_feature
<222> LOCATION: 16-24
<223> OTHER INFORMATION: n = A, T, C or G
<220> FEATURE:
<223> OTHER INFORMATION: Primer

<400> SEQUENCE: 5
gtacgtatga tcatgnnnnn nnnngatgaa ctggtattt                     39

<210> SEQ ID NO 6
<211> LENGTH: 23
<212> TYPE: DNA
<213> ORGANISM: Artificial Sequence
<220> FEATURE:
<223> OTHER INFORMATION: Downstream primer
```

<400> SEQUENCE: 6
gctaattaag cttggctgca ggc  23

<210> SEQ ID NO 7
<211> LENGTH: 24
<212> TYPE: DNA
<213> ORGANISM: Artificial Sequence
<220> FEATURE:
<223> OTHER INFORMATION: Antisense-primer

<400> SEQUENCE: 7
tacatggacc tttacttcga acgc  24

<210> SEQ ID NO 8
<211> LENGTH: 20
<212> TYPE: DNA
<213> ORGANISM: Artificial Sequence
<220> FEATURE:
<223> OTHER INFORMATION: Primer FVL20TH

<400> SEQUENCE: 8
acaaaatacc tgtattcctt  20

<210> SEQ ID NO 9
<211> LENGTH: 90
<212> TYPE: DNA
<213> ORGANISM: Artificial Sequence
<220> FEATURE:
<223> OTHER INFORMATION: Template TFVL90A

<400> SEQUENCE: 9
gacatcatga gagacatcgc ctctgggcta ataggactac ttctaatctg taagagcaga  60
tccctggaca ggcaaggaat acaggtattt  90

<210> SEQ ID NO 10
<211> LENGTH: 90
<212> TYPE: DNA
<213> ORGANISM: Artificial Sequence
<220> FEATURE:
<223> OTHER INFORMATION: Template TFVL90G

<400> SEQUENCE: 10
gacatcatga gagacatcgc ctctgggcta ataggactac ttctaatctg taagagcaga  60
tccctggaca ggcgaggaat acaggtattt  90

<210> SEQ ID NO 11
<211> LENGTH: 20
<212> TYPE: DNA
<213> ORGANISM: Artificial Sequence
<220> FEATURE:
<223> OTHER INFORMATION: Primer for the detection of the SNP in human
    genomic factor V Leiden DNA sequence.
<220> FEATURE:
<221> NAME/KEY: misc_feature
<222> LOCATION: 20
<223> OTHER INFORMATION: n = A, T, C or G

<400> SEQUENCE: 11
acaaaatacc tgtattcctn  20

<210> SEQ ID NO 12
<211> LENGTH: 35
<212> TYPE: DNA
<213> ORGANISM: Artificial Sequence
<220> FEATURE:

```
<223> OTHER INFORMATION: Template of human genomic factor V Leiden DNA
      sequence; n=g, wildtype template; n=a, mutant template
<220> FEATURE:
<221> NAME/KEY: misc_feature
<222> LOCATION: 16
<223> OTHER INFORMATION: n = A, T, C or G

<400> SEQUENCE: 12
gatccctgga caggcnagga atacaggtat tttgt                              35

<210> SEQ ID NO 13
<211> LENGTH: 22
<212> TYPE: DNA
<213> ORGANISM: Artificial sequence
<220> FEATURE:
<223> OTHER INFORMATION: Primer for the detection of human somatic CRAF
      T1769A mutation

<400> SEQUENCE: 13
gacccactcc atcgagattt ct                                            22

<210> SEQ ID NO 14
<211> LENGTH: 35
<212> TYPE: DNA
<213> ORGANISM: Artificial sequence
<220> FEATURE:
<223> OTHER INFORMATION: Wild type template of BRAF gene; w = t, wild
      type template; w = a, mutant template

<400> SEQUENCE: 14
ggtctagcta cagwgaaatc tcgatggagt gggtc                              35

<210> SEQ ID NO 15
<211> LENGTH: 25
<212> TYPE: DNA
<213> ORGANISM: Artificial Sequence
<220> FEATURE:
<223> OTHER INFORMATION: Primer for the detection of human
      dihydropyrimidine dehydrogenase (DpyD) mutation G735A

<400> SEQUENCE: 15
gttttagatg ttaaatcaca cttat                                         25

<210> SEQ ID NO 16
<211> LENGTH: 38
<212> TYPE: DNA
<213> ORGANISM: Artificial Sequence
<220> FEATURE:
<223> OTHER INFORMATION: Template of human DpyD; r=g, wild type
      template; r=a, mutant template

<400> SEQUENCE: 16
ctttccagac aacrtaagtg tgatttaaca tctaaaac                           38

<210> SEQ ID NO 17
<211> LENGTH: 20
<212> TYPE: DNA
<213> ORGANISM: Artificial sequence
<220> FEATURE:
<223> OTHER INFORMATION: Primer for the detection of human acid
      ceramidase mutation A107G

<400> SEQUENCE: 17
cgttggtcct gaaggaggat                                               20

<210> SEQ ID NO 18
<211> LENGTH: 33
```

```
<212> TYPE: DNA
<213> ORGANISM: Artificial sequence
<220> FEATURE:
<223> OTHER INFORMATION: Template of human acid ceramidase; r=a, wild
      type template; r=g, mutant template

<400> SEQUENCE: 18
aaatcaacct rtcctccttc aggaccaacg tac                                 33

<210> SEQ ID NO 19
<211> LENGTH: 22
<212> TYPE: DNA
<213> ORGANISM: Artificial sequence
<220> FEATURE:
<223> OTHER INFORMATION: Primer probe BrafT

<400> SEQUENCE: 19
gacccactcc atcgagattt ct                                             22

<210> SEQ ID NO 20
<211> LENGTH: 22
<212> TYPE: DNA
<213> ORGANISM: Artificial sequence
<220> FEATURE:
<223> OTHER INFORMATION: Reverse primer for BRAF

<400> SEQUENCE: 20
agaggaaaga tgaagtacta tg                                             22

<210> SEQ ID NO 21
<211> LENGTH: 239
<212> TYPE: DNA
<213> ORGANISM: Artificial sequence
<220> FEATURE:
<223> OTHER INFORMATION: Target template BrafX; w = a, Braf A (wild
      type); w = t, BrafT (mutant)

<400> SEQUENCE: 21
caactgttca aactgatggg acccactcca tcgagatttc wctgtagcta gaccaaaatc    60
acctattttt actgtgaggt cttcatgaag aaatatatct gaggtgtagt aagtaaagga   120
aaacagtaga tctcattttc ctatcagagc aagcattatg aagagtttag gtaagagatc   180
taatttctat aattctgtaa tataatattc tttaaaacat agtacttcat ctttcctct    239

<210> SEQ ID NO 22
<211> LENGTH: 25
<212> TYPE: DNA
<213> ORGANISM: Artificial sequence
<220> FEATURE:
<223> OTHER INFORMATION: Primer probe DpyDT

<400> SEQUENCE: 22
gttttagatg ttaaatcaca cttat                                          25

<210> SEQ ID NO 23
<211> LENGTH: 23
<212> TYPE: DNA
<213> ORGANISM: Artificial sequence
<220> FEATURE:
<223> OTHER INFORMATION: Reverse primer for DpyDT

<400> SEQUENCE: 23
aaagctcctt tctgaatatt gag                                            23

<210> SEQ ID NO 24
```

```
<211> LENGTH: 300
<212> TYPE: DNA
<213> ORGANISM: Artificial sequence
<220> FEATURE:
<223> OTHER INFORMATION: Target template DpyDX; n = a, DpyDA (wild
      type); r = t DpyDT (mutant)
<220> FEATURE:
<221> NAME/KEY: misc_feature
<222> LOCATION: 276
<223> OTHER INFORMATION: n = a or t

<400> SEQUENCE: 24
aaaatgtgag aagggacctc ataaaatatg tcatatggaa atgagcagat aataaagatt      60
atagcttttc tttgtcaaaa ggagactcaa tatctttact ctttcatcag acattgtga     120 caaatgtttc ccccagaatc atccggggaa ccacctctgg ccccatgtat ggccctggac    180
aaagctcctt tctgaatatt gagctcatca gtgagaaaac ggctgcatat tggtgtcaaa    240
gtgtcactga actaaaggct gactttccag acaacntaag tgtgatttaa catctaaaac    300

<210> SEQ ID NO 25
<211> LENGTH: 7043
<212> TYPE: DNA
<213> ORGANISM: Artificial sequence
<220> FEATURE:
<223> OTHER INFORMATION: pTTQ18::Taq

<400> SEQUENCE: 25
gaactggatc tcaacagcgg taagatcctt gagagttttc gccccgaaga acgttttcca     60
atgatgagca cttttaaagt tctgctatgt ggcgcggtat tatcccgtat tgacgccggg    120
caagagcaac tcggtcgccg catacactat tctcagaatg acttggttga gtactcacca    180
gtcacagaaa agcatcttac ggatggcatg acagtaagag aattatgcag tgctgccata    240
accatgagtg ataacactgc ggccaactta cttctgacaa cgatcggagg accgaaggag    300
ctaaccgctt ttttgcacaa catgggggat catgtaactc gccttgatcg ttgggaaccg    360
gagctgaatg aagccatacc aaacgacgag cgtgacacca cgatgcctgt agcaatggca    420
acaacgttgc gcaaactatt aactggcgaa ctacttactc tagcttcccg gcaacaatta    480
atagactgga tggaggcgga taaagttgca ggaccacttc tgcgctcggc ccttccggct    540
ggctggttta ttgctgataa atctggagcc ggtgagcgtg ggtctcgcgg tatcattgca    600
gcactggggc cagatggtaa gccctcccgt atcgtagtta tctacacgac ggggagtcag    660
gcaactatgg atgaacgaaa tagacagatc gctgagatag gtgcctcact gattaagcat    720
tggtaactgt cagaccaagt ttactcatat atactttaga ttgatttaaa acttcatttt    780
taatttaaaa ggatctaggt gaagatcctt tttgataatc tcatgaccaa atcccttaa     840 cgtgagtttt cgttccactg agcgtcagac cccgtagaaa agatcaaagg atcttcttga    900
gatccttttt ttctgcgcgt aatctgctgc ttgcaaacaa aaaaaccacc gctaccagcg    960
gtggtttgtt tgccggatca agagctacca actctttttc cgaaggtaac tggcttcagc   1020
agagcgcaga taccaaatac tgtccttcta gtgtagccgt agttaggcca ccacttcaag   1080
aactctgtag caccgcctac atacctcgct ctgctaatcc tgttaccagt ggctgctgcc   1140
agtggcgata agtcgtgtct taccgggttg gactcaagac gatagttacc ggataaggcg   1200
cagcggtcgg gctgaacggg gggttcgtgc acacagccca gcttggagcg aacgacctac   1260
accgaactga gatacctaca gcgtgagcat tgagaaagcg ccacgcttcc cgaagggaga   1320
aaggcggaca ggtatccggt aagcggcagg gtcggaacag gagagcgcac gagggagctt   1380
```

```
ccaggggggaa acgcctggta tctttatagt cctgtcgggt ttcgccacct ctgacttgag    1440
cgtcgatttt tgtgatgctc gtcagggggg cggagcctat ggaaaaacgc cagcaacgcg    1500
gcctttttac ggttcctggc cttttgctgg ccttttgctc acatgttctt tcctgcgtta    1560 tccccctgatt ctgtggataa ccgtattacc gcctttgagt gagctgatac cgctcgccgc    1620
agccgaacga ccgagcgcag cgagtcagtg agcgaggaag cggaagagcg cccaatacgc    1680
aaaccgcctc tccccgcgcg ttggccgatt cattaatgca gaattaattc tcatgtttga    1740
cagcttatca tcgactgcac ggtgcaccaa tgcttctggc gtcaggcagc catcggaagc    1800
tgtggtatgg ctgtgcaggt cgtaaatcac tgcataattc gtgtcgctca aggcgcactc    1860
ccgttctgga taatgttttt tgcgccgaca tcataacggt tctggcaaat attctgaaat    1920
gagctgttga caattaatca tcggctcgta taatgtgtgg aattgtgagc ggataacaat    1980
ttcacacagg aaacagcgat gaattcgggg atgctgcccc tctttgagcc caagggccgg    2040
gtcctcctgg tggacggcca ccacctggcc taccgcacct ccacgccct gaagggcctc    2100 accaccagcc gggggagcc ggtgcaggcg gtctacggct cgccaagag cctcctcaag    2160 gccctcaagg aggacgggga cgcggtgatc gtggtctttg acgccaaggc cccctccttc    2220
cgccacgagg cctacggggg gtacaaggcg ggccgggccc ccacgccgga ggactttccc    2280
cggcaactcg ccctcatcaa ggagctggtg gacctcctgg ggctggcgcg cctcgaggtc    2340
ccgggctacg aggcggacga cgtcctggcc agcctggcca agaaggcgga aaaggagggc    2400
tacgaggtcc gcatcctcac cgccgacaaa gacctttacc agctcctttc cgaccgcatc    2460
cacgtcctcc accccgaggg gtacctcatc accccggcct ggctttggga aaagtacggc    2520
ctgaggcccg accagtgggc cgactaccgg gccctgaccg ggacgagtc cgacaacctt    2580 cccgggtca agggcatcgg ggagaagacg gcgaggaagc ttctggagga gtgggggagc    2640
ctggaagccc tcctcaagaa cctggaccgg ctgaagcccg ccatccggga agatcctg    2700 gcccacatgg acgatctgaa gctctcctgg gacctggcca aggtgcgcac cgacctgccc    2760
ctggaggtgg acttcgccaa aaggcgggag cccgaccggg agaggcttag ggccttctg    2820 gagaggcttg agtttggcag cctcctccac gagttcggcc ttctggaaag ccccaaggcc    2880
ctggaggagg cccctggcc cccgccggaa ggggccttcg tgggctttgt gctttccgc    2940 aaggagccca tgtgggccga tcttctggcc ctggccgccg ccagggggg ccgggtccac    3000 cgggcccccg agccttataa agccctcagg gacctgaagg aggcgcgggg gcttctcgcc    3060
aaagacctga gcgttctggc cctgagggaa ggccttggcc tccgccccgg cgacgacccc    3120
atgctcctcg cctacctcct ggacccttcc aacaccaccc ccgagggggt ggcccggcgc    3180 tacgcgggg agtggacgga ggaggcgggg agcgggccg cccttttccga gaggctcttc    3240 gccaacctgt gggggaggct tgaggggag gagaggctcc tttggcttta ccgggaggtg    3300
gagaggcccc tttccgctgt cctgcccac atggaggcca ggggtgcg cctgacgtg    3360 gcctatctca gggccttgtc cctggaggtg gccgaggaga tcgcccgcct cgaggccgag    3420
gtcttccgcc tggccggcca ccccttcaac ctcaactccc gggaccagct ggaaagggtc    3480
ctctttgacg agctagggct tccgccatc ggcaagacgg agaagaccgg caagcgctcc    3540
accagcgccg ccgtcctgga ggccctccgc gaggccacc ccatcgtgga aagatcctg    3600 cagtaccggg agctcaccaa gctgaagagc acctacattg accccttgcc ggacctcatc    3660 cacccccagga cggccgcct ccacacccgc ttcaaccaga cggccacggc cacgggcagg    3720
ctaagtagct ccgatcccaa cctccagaac atccccgtcc gcaccccgct tgggcagagg    3780
```

```
atccgccggg ccttcatcgc cgaggagggg tggctattgg tggccctgga ctatagccag   3840
atagagctca gggtgctggc ccacctctcc ggcgacgaga acctgatccg ggtcttccag   3900
gaggggcggg acatccacac ggagaccgcc agctggatgt tcggcgtccc ccgggaggcc   3960 gtggacccce tgatgcgccg gcggccaag accatcaact tcggggtcct ctacggcatg    4020
tcggcccacc gcctctccca ggagctagcc atcccttacg aggaggccca ggccttcatt   4080
gagcgctact ttcagagctt ccccaaggtg cgggcctgga ttgagaagac cctggaggag   4140
ggcaggaggc gggggtacgt ggagaccctc ttcggccgcc gccgctacgt gccagaccta   4200
gaggcccggg tgaagagcgt gcgggaggcg gccgagcgca tggccttcaa catgcccgtc   4260
cagggcaccg ccgccgacct catgaagctg gctatggtga agctcttccc caggctggag   4320
gaaatggggg ccaggatgct ccttcaggtc cacgacgagc tggtcctcga ggccccaaaa   4380
gagagggcgg aggccgtggc ccggctggcc aaggaggtca tggaggggt gtatcccctg    4440 gccgtgcccc tggaggtgga ggtggggata ggggaggact ggctctccgc caaggagtga   4500
tagatcctct agagtcgacc tgcaggcatg caagcttggc actggccgtc gttttacaac   4560
gtcgtgactg ggaaaaccct ggcgttaccc aacttaatcg ccttgcagca catccccctt   4620
tcgccagctg gcgtaatagc gaagaggccc gcaccgatcg cccttcccaa cagttgcgca   4680
gcctgaatgg cgaatggcgc ctgatgcggt attttctcct tacgcatctg tgcggtattt   4740
cacaccgcat aaattccctg ttttggcgga tgagagaaga ttttcagcct gatacagatt   4800
aaatcagaac gcagaagcgg tctgataaaa cagaatttgc ctggcggcag tagcgcggtg   4860
gtcccacctg accccatgcc gaactcagaa gtgaaacgcc gtagcgccga tggtagtgtg   4920
gggtctcccc atgcgagagt agggaactgc caggcatcaa ataaaacgaa aggctcagtc   4980
gaaagactgg gcctttcgtt ttatctgttg tttgtcggtg aacgctctcc tgagtaggac   5040
aaatccgccg ggagcggatt tgaacgttgc gaagcaacgg cccggagggt ggcgggcagg   5100
acgcccgcca taaactgcca ggcatcaaat taagcagaag gccatcctga cggatggcct   5160
ttttgcgttt ctacaaactc ttcctgtcgt catatctaca agccatcccc ccacagatac   5220
ggtaaactag cctcgttttt gcatcaggaa agcagggaat ttatggtgca ctctcagtac   5280
aatctgctct gatgccgcat agttaagcca gccccgacac ccgccaacac ccgctgacgc   5340
gccctgacgg gcttgtctgc tcccggcatc cgcttacaga caagctgtga ccgtctccgg   5400
gagctgcatg tgtcagaggt tttcaccgtc atcaccgaaa cgcgcgagac gaaagggcct   5460
cgtgatacgc ctatttttat aggttaatgt catgataata atggtttctt agacgtgagg   5520
ttctgtaccc gacaccatcg aatggtgcaa aacctttcgc ggtatggcat gatagcgccc   5580
ggaagagagt caattcaggg tggtgaatgt gaaaccagta acgttatacg atgtcgcaga   5640
gtatgccggt gtctcttatc agaccgtttc ccgcgtggtg aaccaggcca gccacgtttc   5700
tgcgaaaacg cgggaaaaag tggaagcggc gatggcggag ctgaattaca ttcccaaccg   5760
cgtggcacaa caactggcgg gcaaacagtc gttgctgatt ggcgttgcca cctccagtct   5820
ggccctgcac gcgccgtcgc aaattgtcgc ggcgattaaa tctcgcgccg atcaactggg   5880
tgccagcgtg gtggtgtcga tggtagaacg aagcggcgtc gaagcctgta aagcggcggt   5940
gcacaatctt ctcgcgcaac gcgtcagtgg gctgatcatt aactatccgc tggatgacca   6000
ggatgccatt gctgtggaag ctgcctgcac taatgttccg gcgttatttc ttgatgtctc   6060
tgaccagaca cccatcaaca gtattatttt ctcccatgaa gacggtacgc gactgggcgt   6120
```

```
ggagcatctg gtcgcattgg gtcaccagca aatcgcgctg ttagcgggcc cattaagttc    6180
tgtctcggcg cgtctgcgtc tggctggctg gcataaatat ctcactcgca atcaaattca    6240
gccgatagcg gaacgggaag gcgactggag tgccatgtcc ggttttcaac aaaccatgca    6300
aatgctgaat gagggcatcg ttcccactgc gatgctggtt gccaacgatc agatggcgct    6360
gggcgcaatg cgcgccatta ccgagtccgg gctgcgcgtt ggtgcggata tctcggtagt    6420
gggatacgac gataccgaag acagctcatg ttatatcccg ccgttaacca ccatcaaaca    6480
ggattttcgc ctgctggggc aaaccagcgt ggaccgcttg ctgcaactct ctcagggcca    6540
ggcggtgaag ggcaatcagc tgttgcccgt ctcactggtg aaaagaaaaa ccaccctggc    6600
gcccaatacg caaaccgcct ctccccgcgc gttggccgat tcattaatgc agctggcacg    6660
acaggtttcc cgactggaaa gcgggcagtg agcgcaacgc aattaatgta agttagctca    6720
ctcattaggc accccaggct ttacacttta tgcttccgac ctgcaagaac ctcacgtcag    6780
gtggcacttt tcggggaaat gtgcgcggaa cccctatttg tttatttttc taaatacatt    6840
caaatatgta tccgctcatg agacaataac cctgataaat gcttcaataa tattgaaaaa    6900
ggaagagtat gagtattcaa catttccgtg tcgcccttat tcccttttt  gcggcatttt    6960 gccttcctgt ttttgctcac ccagaaacgc tggtgaaagt aaaagatgct gaagatcagt    7020
tgggtgcacg agtgggttac atc                                           7043
```

<210> SEQ ID NO 26
<211> LENGTH: 10534
<212> TYPE: DNA
<213> ORGANISM: Artificial sequence
<220> FEATURE:
<223> OTHER INFORMATION: pQE30

<400> SEQUENCE: 26

```
ctcgagaaat cataaaaaat ttatttgctt tgtgagcgga taacaattat aatagattca      60
attgtgagcg gataagagct ctttagtatt ttttaaataa cgaaacact  cgcctattgt     120 taatattatc taagttaaca ctcgcctatt caatttcaca cagaattcat taagaggag      180 aaattaacta tgagaggatc gcatcaccat caccatcacg gatccgttaa agtgtgtctt     240
aagtaatttc tcctctttaa ttgatactct cctagcgtag tggtagtggt agtgcctagg     300
acggcaacgg tgatttctta tgacaactac gtcaccatcc ttgatgaaga acactgaaa      360 gcgtggattg cgaagtgccg ttgccactaa agaatactgt tgatgcagtg gtaggaacta     420
cttctttgtg actttcgcac ctaacgcttc ctggaaaaag cgccggtatt tgcatttgat     480
accgaaaccg acagccttga taacatctct gctaacctgg tcggggacct ttttcgcggc     540
cataaacgta aactatggct ttggctgtcg gaactattgt agagacgatt ggaccagccc     600 ctttctttg  ctatcgagcc aggcgtagcg gcatatattc cggttgctca tgattatctt     660
gatgcgcccg atcaagaaag aaaacgatag ctcggtccgc atcgccgtat ataaggccaa     720
cgagtactaa tagaactacg cgggctagtt atctctcgcg agcgtgcact cgagttgcta     780
aaaccgctgc tggaagatga aaaggcgctg aaggtcgggc aaaactagag agcgctcgca     840
cgtgagctca acgatttggg cgacgacctt ctacttttcc gcgacttcca gcccgttttg     900
ctgaaatacg atcgcggtat tctggcgaac tacggcattg aactgcgtgg gattgcgttt     960
gataccatgc tggaggactt tatgctagcg ccataagacc gcttgatgcc gtaacttgac    1020
gcaccctaac gcaaactatg gtacgacctc tcctacattc tcaatagcgt tgccgggcgt    1080
cacgatatgg acagcctcgc ggaacgttgg ttgaagcaca aaaccaggat gtaagagtta    1140
```

```
tcgcaacggc ccgcagtgct atacctgtcg gagcgccttg caaccaactt cgtgttttgg    1200 atcactttg  aagagattgc tggtaaaggc aaaaatcaac tgacctttaa ccagattgcc    1260
ctcgaagaag ccggatagtg aaaacttctc taacgaccat ttccgttttt agttgactgg    1320
aaattggtct aacgggagct tcttcggcct cgttacgccg ccgaagatgc agatgtcacc    1380
ttgcagttgc atctgaaaat gtggccggat ctgcaaaaac acaaagcaat gcggcggctt    1440
ctacgtctac agtggaacgt caacgtagac ttttacaccg gcctagacgt ttttgtgttt    1500
gggccgttga acgtcttcga gaatatcgaa atgccgctgg tgccggtgct ttcacgcatt    1560
gaacgtaacg gtgtgcccgg caacttgcag aagctcttat agctttacgg cgaccacggc    1620
cacgaaagtg cgtaacttgc attgccacac aagatcgatc cgaaagtgct gcacaatcat    1680
tctgaagagc tcacccttcg tctggctgag ctggaaaaga aagcgttcta gctaggcttt    1740
cacgacgtgt tagtaagact tctcgagtgg gaagcagacc gactcgacct tttctttcgc    1800
catgaaattg caggtgagga atttaacctt tcttccacca agcagttaca aaccattctc    1860
tttgaaaaac agggcgtact ttaacgtcca ctccttaaat tggaagaag  gtggttcgtc    1920 aatgtttggt aagagaaact ttttgtcccg attaaaccgc tgaagaaaac gccgggtggc    1980
gcgccgtcaa cgtcggaaga ggtactggaa gaactggcgc tggactaatt tggcgacttc    2040
ttttgcggcc caccgcgcgg cagttgcagc cttctccatg accttcttga ccgcgacctg    2100
tatccgttgc caaaagtgat tctggagtat cgtggtctgg cgaagctgaa atcgacctac    2160
accgacaagc tgccgatagg caacggtttt cactaagacc tcatagcacc agaccgcttc    2220
gactttagct ggatgtggct gttcgacggc ctgatgatca cccgaaaac  cgggcgtgtg    2280 catacctctt atcaccaggc agtaactgca acgggacgtt tatcggacta ctagttgggc    2340
ttttggcccg cacacgtatg gagaatagtg gtccgtcatt gacgttgccc tgcaaatagc    2400
tcaaccgatc ctaacctgca aaacattccg gtgcgtaacg aagaaggtcg tcgtatccgc    2460
caggcgttta ttgcgagttg gctaggattg gacgttttgt aaggccacgc attgcttctt    2520
ccagcagcat aggcggtccg caaataacgc ccagaggatt atgtgattgt ctcagcggac    2580
tactcgcaga ttgaactgcg cattatggcg catctttcgc gtgacggtct cctaatacac    2640
taacagagtc gcctgatgag cgtctaactt gacgcgtaat accgcgtaga agcgcactg    2700 aaaggcttgc tgaccgcatt cgcggaagga aaagatatcc accgggcaac ggcggcagaa    2760
gtgtttggtt tgccatttcc gaacgactgg cgtaagcgcc ttccttttct ataggtggcc    2820 cgttccgcc  gtcttcacaa accaaacggt ctggaaaccg tcaccagcga gcaacgccgt    2880
agcgcgaaag cgatcaactt tggtctgatt tatggcatga gtgctgacct ttggcagtgg    2940
tcgctcgttg cggcatcgcg ctttcgctag ttgaaaccag actaaatacc gtactcacga    3000
ttcggtctgg cgcggcaatt gaacattcca cgtaaagaag cgcagaagta catggacctt    3060
tacttcgaac gctacaagcc agaccgcgcc gttaacttgt aaggtgcatt tcttcgcgtc    3120
ttcatgtacc tggaaatgaa gcttgcgatg cctggcgtgc tggagtatat ggaacgcacc    3180
cgtgctcagg cgaaagagca gggctacgtt gaaacgctgg acggaggacc gcacgacctc    3240
atataccttg cgtgggcacg agtccgcttt ctcgtcccga tgcaactttg cgacctgcct    3300
cgccgtctgt atctgccgga tatcaaatcc agcaatggtg ctcgtcgtgc agcggctgaa    3360
cgtgcagcca ttaacgcggc agacatagac ggcctatagt ttaggtcgtt accacgagca    3420
gcacgtcgcc gacttgcacg tcggtaattg gcgccaatgc agggaaccgc cgccgacatt    3480
```

-continued

```
atcaaacggg cgatgattgc cgttgatgcg tggttacagg ctgagcgcgg ttacgtccct    3540
tggcggcggc tgtaatagtt tgcccgctac taacggcaac tacgcaccaa tgtccgactc    3600
caaccgcgtg tacgtatgat catgcaggta cacgatgaac tggtatttga agttcataaa    3660
gatgatgttg atgccgttgg cgcacatgca tactagtacg tccatgtgct acttgaccat    3720
aaacttcaag tatttctact acaactacgg gtcgcgaagc agattcatca actgatggaa    3780
aactgtaccc gtctggatgt gccgttgctg gtggaagtgg ggagtcagcg cttcgtctaa    3840
gtagttgact accttttgac atgggcagac ctacacggca acgaccacct tcacccctca    3900
ggcgaaaact gggatcaggc gcactaagat tcgcctgcag ccaagcttaa ttagctgagc    3960
ttggactcct gttgaccgct tttgaccctta gtccgcgtga ttctaagcgg acgtcggttc    4020
gaattaatcg actcgaacct gaggacaact tagatccagt aatgacctca gaactccatc    4080
tggatttgtt cagaacgctc ggttgccgcc gggcgttttt tattgatcta ggtcattact    4140
ggagtcttga ggtagaccta acaagtcctt gcgagccaac ggcggcccgc aaaaaataac    4200
gtgagaatcc aagctagctt ggcgagattt tcaggagcta aggaagctaa aatggagaaa    4260
aaaatcactg gatatcactc ttaggttcga tcgaaccgct ctaaaagtcc tcgattcctt    4320
cgattttacc tcttttttta gtgacctata accaccgttg atatatccca atggcatcgt    4380
aaagaacatt ttgaggcatt tcagtcagtt gctcaatgta cctattggtg caactatat    4440 agggttaccg tagcatttct tgtaaaactc cgtaaagtca gtcaacgagt tacatggata    4500
aaccagaccg ttcagctgga tattacggcc ttttttaaaga ccgtaaagaa aaataagcac    4560
aagttttatc cggccttggt ctggcaagtc gacctataat gccggaaaaa tttctggcat    4620 ttcttttttat tcgtgttcaa aataggccgg tttattcaca ttcttgcccg cctgatgaat    4680
gctcatccgg aatttcgtat ggcaatgaaa gacggtgagc tggtgaaata agtgtaagaa    4740
cgggcggact acttacgagt aggccttaaa gcataccgtt actttctgcc actcgaccac    4800
atatgggata gtgttcaccc ttgttacacc gttttccatg agcaaactga acgttttca    4860 tcgctctgga gtgaatatac cctatcacaa gtgggaacaa tgtggcaaaa ggtactcgtt    4920
tgactttgca aaagtagcga gacctcactt taccacgacg atttccggca gtttctacac    4980
atatattcgc aagatgtggc gtgttacggt gaaaacctgg cctatatggt gctgctaaag    5040
gccgtcaaag atgtgtatat aagcgttcta caccgcacaa tgccacttttt ggaccggata    5100 ttccctaaag ggtttattga gaatatgttt ttcgtctcag ccaatccctg ggtgagtttc    5160
accagttttg atttaaaggg gatttcccaaa taactcttat acaaaaagca gagtcggtta    5220
gggacccact caaagtggtc aaaactaaat aacgtggcca atatggacaa cttcttcgcc    5280
cccgttttca ccatgggcaa atattatacg caaggcgaca aggtgttgca ccggttatac    5340
ctgttgaaga agcgggggca aaagtggtac ccgtttataa tatgcgttcc gctgttccac    5400
ctgatgccgc tggcgattca ggttcatcat gccgtttgtg atggcttcca tgtcggcaga    5460
atgcttaatg aattagacta cggcgaccgc taagtccaag tagtacggca aacactaccg    5520
aaggtacagc cgtcttacga attacttaat caacagtact gcgatgagtg gcagggcggg    5580
gcgtaatttt tttaaggcag ttattggtgc ccttaaacgc ctggggttgt catgacgcta    5640
ctcaccgtcc cgccccgcat taaaaaaatt ccgtcaataa ccacgggaat ttgcggaccc    5700
gtaatgactc tctagcttga ggcatcaaat aaaacgaaag gctcagtcga aagactgggc    5760 cttttcgtttt atctgcatta ctgagagatc gaactccgta gtttattttg ctttccgagt    5820
cagctttctg acccggaaag caaaatagac ttgtttgtcg gtgaacgctc tcctgagtag    5880
```

```
gacaaatccg ccctctagag ctgcctcgcg cgtttcggtg atgacaacaa acagccactt      5940
gcgagaggac tcatcctgtt taggcgggag atctcgacgg agcgcgcaaa gcccactactg     6000 ggtgaaaacc tctgacacat gcagctcccg gagacggtca cagcttgtct gtaagcggat     6060
gccgggagca gacaaccact tttggagact gtgtacgtcg agggcctctg ccagtgtcga     6120
acagacattc gcctacggcc ctcgtctgtt gcccgtcagg gcgcgtcagc gggtgttggc     6180
gggtgtcggg gcgcagccat gacccagtca cgtagcgata gcggacgggc agtcccgcgc     6240
agtcgcccac aaccgcccac agcccgcgt cggtactggg tcagtgcatc gctatcgcct      6300
gtgtatactg gcttaactat gcggcatcag agcagattgt actgagagtg caccatatgc     6360
ggtgtgaaat accgccacat atgaccgaat tgatacgccg tagtctcgtc taacatgact     6420
ctcacgtggt atacgccaca ctttatggcg acagatgcg aaggagaaaa taccgcatca      6480
ggcgctcttc cgcttcctcg ctcactgact cgctgcgctc ggtcgtgtct acgcattcct     6540
cttttatggc gtagtccgcg agaaggcgaa ggagcgagtg actgagcgac gcgagccagc     6600
ttcggctgcg gcgagcggta tcagctcact caaaggcggt aatacggtta ccacagaat      6660 caggggataa cgcagaagcc gacgccgctc gccatagtcg agtgagtttc gccattatg      6720 ccaataggtg tcttagtccc ctattgcgtc gaaagaacat gtgagcaaaa ggccagcaaa     6780
aggccaggaa ccgtaaaaag gccgcgttgc tggcgttttt ccatactttc ttgtacactc     6840
gttttccggt cgttttccgg tccttggcat ttttccggcg caacgaccgc aaaaaggtat     6900
ggctccgccc cctgacgag catcacaaaa atcgacgctc aagtcagagg tggcgaaacc      6960
cgacaggact ataaaccgag gcgggggac tgctcgtagt gttttagct gcgagttcag       7020 tctccaccgc tttgggctgt cctgatattt gataccaggc gtttccccct ggaagctccc     7080
tcgtgcgctc tcctgttccg accctgccgc ttaccggata cctgtctatg gtccgcaaag     7140
ggggaccttc gagggagcac gcgagaggac aaggctggga cggcgaatgg cctatggaca     7200
ccgcctttct cccttcggga agcgtggcgc tttctcatag ctcacgctgt aggtatctca     7260
gttcggtgta ggtcgggcgg aaagagggaa gcccttcgca ccgcgaaaga gtatcgagtg     7320
cgacatccat agagtcaagc cacatccagc ttcgctccaa gctgggctgt gtgcacgaac     7380 ccccgttca gcccgaccgc tgcgccttat ccggtaacta tcgtcaagcg aggttcgacc      7440
cgacacacgt gcttgggggg caagtcgggc tggcgacgcg gaataggcca ttgatagcag     7500
ttgagtccaa cccggtaaga cacgacttat cgccactggc agcagccact ggtaacagga     7560
ttagcagagc gaggtaactc aggttgggcc attctgtgct gaatagcggt gaccgtcgtc     7620
ggtgaccatt gtcctaatcg tctcgctcca atgtaggcgg tgctacagag ttcttgaagt     7680
ggtggcctaa ctacggctac actagaagga cagtatttgg tatcttacat ccgccacgat     7740
gtctcaagaa cttcaccacc ggattgatgc cgatgtgatc ttcctgtcat aaaccataga     7800
gcgctctgct gaagccagtt accttcggaa aaagagttgg tagctcttga tccggcaaac     7860
aaaccaccgc tggtacgcga gacgacttcg gtcaatggaa gccttttctc aaccatcga     7920 gaactaggcc gtttgtttgg tggcgaccat gcggtggttt ttttgtttgc aagcagcaga     7980
ttacgcgcag aaaaaaagga tctcaagaag atcctttgat cttttcgcca ccaaaaaac     8040 aaacgttcgt cgtctaatgc gcgtcttttt ttcctagagt tcttctagga aactagaaaa     8100
ctacggggtc tgacgctcag tggaacgaaa actcacgtta agggattttg gtcatgagat     8160
tatcaaaaag gatctgatgc cccagactgc gagtcacctt gcttttgagt gcaattccct     8220
```

```
aaaaccagta ctctaatagt tttccctaga tcacctagat ccttttaaat taaaaatgaa    8280
gttttaaatc aatctaaagt atatatgagt aaacttggtc tgacaagtgg atctaggaaa    8340
atttaatttt tacttcaaaa tttagttaga tttcatatat actcatttga accagactgt    8400
gttaccaatg cttaatcagt gaggcaccta tctcagcgat ctgtctattt cgttcatcca    8460
tagttgcctg actcccaatg gttacgaatt agtcactccg tggatagagt cgctagacag    8520
ataaagcaag taggtatcaa cggactgagg ccgtcgtgta gataactacg atacgggagg    8580
gcttaccatc tggccccagt gctgcaatga taccgcgaga cccacggcag cacatctatt    8640
gatgctatgc cctcccgaat ggtagaccgg ggtcacgacg ttactatggc gctctgggtg    8700
gctcaccggc tccagattta tcagcaataa accagccagc cggaagggcc gagcgcagaa    8760
gtggtcctgc aacttcgagt ggccgaggtc taaatagtcg ttatttggtc ggtcggcctt    8820
cccggctcgc gtcttcacca ggacgttgaa tatccgcctc catccagtct attaattgtt    8880
gccgggaagc tagagtaagt agttcgccag ttaatagttt gcgcaatagg cggaggtagg    8940
tcagataatt aacaacggcc cttcgatctc attcatcaag cggtcaatta tcaaacgcgt    9000
acgttgttgc cattgctaca ggcatcgtgg tgtcacgctc gtcgtttggt atggcttcat    9060
tcagctccgg ttccctgcaa caacggtaac gatgtccgta gcaccacagt gcgagcagca    9120
aaccataccg aagtaagtcg aggccaaggg aacgatcaag gcgagttaca tgatccccca    9180
tgttgtgcaa aaaagcggtt agctccttcg gtcctccgat cgttgttgct agttccgctc    9240
aatgtactag ggggtacaac acgttttttc gccaatcgag gaagccagga ggctagcaac    9300
tcagaagtaa gttggccgca gtgttatcac tcatggttat ggcagcactg cataattctc    9360
ttactgtcat gccatagtct tcattcaacc ggcgtcacaa tagtgagtac caataccgtc    9420
gtgacgtatt aagagaatga cagtacggta ccgtaagatg cttttctgtg actggtgagt    9480
actcaaccaa gtcattctga gaatagtgta tgcggcgacc gagttggcat tctacgaaaa    9540
gacactgacc actcatgagt tggttcagta agactcttat cacatacgcc gctggctcaa    9600
gctcttgccc ggcgtcaata cgggataata ccgcgccaca tagcagaact ttaaaagtgc    9660
tcatcattgg aaaaccgaga acgggccgca gttatgccct attatggcgc ggtgtatcgt    9720
cttgaaattt tcacgagtag taaccttttg gttcttcggg gcgaaaactc tcaaggatct    9780
taccgctgtt gagatccagt tcgatgtaac ccactcgtgc acccacaaga agccccgctt    9840
ttgagagttc ctagaatggc gacaactcta ggtcaagcta cattgggtga gcacgtgggt    9900
actgatcttc agcatctttt actttccacca gcgtttctgg gtgagcaaaa acaggaaggc    9960
aaaatgccgc aaaaatgact agaagtcgta gaaaatgaaa gtggtcgcaa agacccactc   10020
gttttgtcc ttccgtttta cggcgttttt agggaataag ggcgacacgg aaatgttgaa   10080
tactcatact cttccttttt caatattatt gaagcattta tcaggtccct tattcccgct   10140
gtgcctttac aacttatgag tatgagaagg aaaaagttat aataacttcg taaatagtcc   10200
gttattgtct catgagcgga tacatatttg aatgtattta gaaaaataaa caataggggg   10260
ttccgcgcac atttccaata acagagtact cgcctatgta taaacttaca taaatctttt   10320
tatttgttta tccccaaggc gcgtgtaaag cccgaaaagt gccacctgac gtctaagaaa   10380
ccattattat catgacatta acctataaaa ataggcgtat cacgagggct tttcacggtg   10440
gactgcagat tctttggtaa taatagtact gtaattggat attttttatcc gcatagtgct   10500
ggcccttccg tcttcacccg ggaaagcaga agtg                              10534
```

-continued

```
<210> SEQ ID NO 27
<211> LENGTH: 11
<212> TYPE: DNA
<213> ORGANISM: Artificial sequence
<220> FEATURE:
<223> OTHER INFORMATION: Template segment (SEQ ID NO:14); w = t,
      wild type; w = a, mutant template

<400> SEQUENCE: 27
ctaaagwgac a                                                         11

<210> SEQ ID NO 28
<211> LENGTH: 11
<212> TYPE: DNA
<213> ORGANISM: Artificial sequence
<220> FEATURE:
<223> OTHER INFORMATION: Template segment (SEQ ID NO: 16); r = g,
      wild type; r = a, mutant

<400> SEQUENCE: 28
gtgaatrcaa c                                                         11

<210> SEQ ID NO 29
<211> LENGTH: 11
<212> TYPE: DNA
<213> ORGANISM: Artificial sequence
<220> FEATURE:
<223> OTHER INFORMATION: Template segment (SEQ ID NO: 12; n = t,
      wild type; n = a, mutant
<220> FEATURE:
<221> NAME/KEY: misc_feature
<222> LOCATION: 7
<223> OTHER INFORMATION: n = a or t

<400> SEQUENCE: 29
taaggancgg a                                                         11

<210> SEQ ID NO 30
<211> LENGTH: 35
<212> TYPE: DNA
<213> ORGANISM: Artificial Sequence
<220> FEATURE:
<223> OTHER INFORMATION: Template of human genomic factor V Leiden DNA
      sequence; n=g, wildtype template

<400> SEQUENCE: 30
gatccctgga caggcgagga atacaggtat tttgt                               35

<210> SEQ ID NO 31
<211> LENGTH: 35
<212> TYPE: DNA
<213> ORGANISM: Artificial Sequence
<220> FEATURE:
<223> OTHER INFORMATION: Template of human genomic factor V Leiden DNA
      sequence; n=a, mutant template

<400> SEQUENCE: 31
gatccctgga caggcaagga atacaggtat tttgt                               35

<210> SEQ ID NO 32
<211> LENGTH: 35
<212> TYPE: DNA
<213> ORGANISM: Artificial sequence
<220> FEATURE:
<223> OTHER INFORMATION: Wild type template of BRAF gene; w = t, wild
      type template

<400> SEQUENCE: 32
```

```
ggtctagcta cagtgaaatc tcgatggagt gggtc                               35
```

<210> SEQ ID NO 33
<211> LENGTH: 35
<212> TYPE: DNA
<213> ORGANISM: Artificial sequence
<220> FEATURE:
<223> OTHER INFORMATION: Wild type template of BRAF gene; w = a, mutant
      template

<400> SEQUENCE: 33

```
ggtctagcta cagagaaatc tcgatggagt gggtc                               35
```

<210> SEQ ID NO 34
<211> LENGTH: 38
<212> TYPE: DNA
<213> ORGANISM: Artificial Sequence
<220> FEATURE:
<223> OTHER INFORMATION: Template of human DpyD; r=g, wild type template

<400> SEQUENCE: 34

```
ctttccagac aacgtaagtg tgatttaaca tctaaaac                            38
```

<210> SEQ ID NO 35
<211> LENGTH: 38
<212> TYPE: DNA
<213> ORGANISM: Artificial Sequence
<220> FEATURE:
<223> OTHER INFORMATION: Template of human DpyD; r=a, mutant template

<400> SEQUENCE: 35

```
ctttccagac aacataagtg tgatttaaca tctaaaac                            38
```

<210> SEQ ID NO 36
<211> LENGTH: 33
<212> TYPE: DNA
<213> ORGANISM: Artificial sequence
<220> FEATURE:
<223> OTHER INFORMATION: Template of human acid ceramidase; r=a, wild
      type template

<400> SEQUENCE: 36

```
aaatcaacct atcctccttc aggaccaacg tac                                 33
```

<210> SEQ ID NO 37
<211> LENGTH: 33
<212> TYPE: DNA
<213> ORGANISM: Artificial sequence
<220> FEATURE:
<223> OTHER INFORMATION: Template of human acid ceramidase;  r=g, mutant
      template

<400> SEQUENCE: 37

```
aaatcaacct gtcctccttc aggaccaacg tac                                 33
```

<210> SEQ ID NO 38
<211> LENGTH: 8
<212> TYPE: PRT
<213> ORGANISM: Artificial Sequence
<220> FEATURE:
<223> OTHER INFORMATION: Family A DNA polymerase motif

<400> SEQUENCE: 38

```
Asp Tyr Ser Gln Ile Glu Leu Arg
  1               5
```